(12) United States Patent
Schmitt et al.

(10) Patent No.: US 7,927,819 B2
(45) Date of Patent: *Apr. 19, 2011

(54) METHOD FOR STABILIZATION OF PROTEINS IN SOLUTION

(75) Inventors: Jacky Schmitt, Kunheim (FR); Matthias Herkert, Heidelberg (DE); Michael Oed, Rodgau (DE)

(73) Assignee: MTM Laboratories, AG, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/710,997

(22) Filed: Feb. 23, 2010

(65) Prior Publication Data

US 2010/0167323 A1    Jul. 1, 2010

Related U.S. Application Data

(63) Continuation of application No. 11/701,522, filed on Jan. 31, 2007, now Pat. No. 7,745,145.

(30) Foreign Application Priority Data

Feb. 3, 2006   (EP) .................................... 06101298

(51) Int. Cl.
G01N 33/53 (2006.01)
(52) U.S. Cl. ......... 435/7.1; 435/7.2; 435/7.91; 435/7.92
(58) Field of Classification Search .................. None
See application file for complete search history.

(56) References Cited

U.S. PATENT DOCUMENTS

| 5,965,454 | A | 10/1999 | Farmilo et al. |
| 7,306,926 | B2 | 12/2007 | Doeberitz et al. |
| 2004/0132113 | A1 | 7/2004 | Nagy |
| 2005/0048602 | A1 | 3/2005 | Takeuchi et al. |
| 2005/0084924 | A1 | 4/2005 | Shults et al. |
| 2007/0037207 | A1 | 2/2007 | Tachikawa et al. |

FOREIGN PATENT DOCUMENTS

| DE | 4239232 A1 | 5/1994 |
| EP | 0185870 A2 | 7/1986 |
| EP | 1388734 | 11/2004 |
| WO | WO03005766 | 12/2003 |

OTHER PUBLICATIONS

Kella N K D et al: "Effect of cetyltrimethylammonium bromide on the heat-induced denaturation and protein-protein interactions of arachin at pH 3.6", Int. Journal of Peptide and Protein Research, vol. 26, No. 2, 1985, pp. 179-186, XP009069323, *abstract*, *pp. 179-181*.

Kella N K D et al: "Effect of sodium dodecyl sulfate on the heat denaturation and aggregation of arachin at pH 3.6" Int. Journal of Peptide and Protein Research, vol. 25, No. 3, 1985, pp. 308-315, XP009069322, *pp. 308-310*.

*Primary Examiner* — Jacob Cheu
(74) *Attorney, Agent, or Firm* — Perkins Coie LLP; Viola T. Kung

(57) ABSTRACT

The present invention relates to a method for stabilization of analytes in solutions of solubilized body samples. The method comprises the steps of solubilizing the body samples obtained from a subject in a suitable sample medium and stabilizing said body sample contained within the sample medium by heating said sample medium for a certain period of time. A further aspect of the invention is a method of a denaturing immunoassay of proteins in solution. The method comprises the steps of bringing a sample containing proteins into contact with a denaturing agent and heating said sample in the presence of the denaturing agent to allow the protein to be denatured.

25 Claims, 11 Drawing Sheets

METHOD FOR STABILIZATION OF PROTEINS IN SOLUTION

This application is a continuation of U.S. patent application Ser. No. 11/701,522, filed Jan. 31, 2007, now U.S. Pat. No. 7,745,145; which claims foreign priority under 119(a)-(d) of EP Application No. 06101298.5, filed Feb. 3, 2006. The above applications are incorporated herein by reference in their entirety.

FIELD OF THE INVENTION

The present invention relates to a method for stabilization of analytes in solutions of solubilized body samples. The method comprises the steps of solubilizing the body samples obtained from a subject in a suitable sample medium and stabilizing said body sample contained within the sample medium by heating said sample medium for a certain period of time. A further aspect of the invention is a method of a denaturing immunoassay of proteins in solution. The method comprises the steps of bringing a sample containing proteins into contact with a denaturing agent and heating said sample in the presence of the denaturing agent to allow the protein to be denatured.

BACKGROUND OF THE INVENTION

In medical diagnosis, one crucial step influencing the results of a diagnostic method applied is the storage and transportation of the sample. This is especially due to the fact that the analytes that are to be detected within a body sample may be subject to degradation or may otherwise be influenced during the transport and storage. In order to ensure accurate determination of diagnostically relevant analytes the integrity of such analytes within the samples must be maintained until analysis is performed.

In the art, one approach to overcome stability problems for analytes seeks to avoid any transportation and storage of samples by implementing point of care testing systems that allow for analysis of body samples directly at the site of patient care, where the sample has been obtained. However, such approaches are limited respective the analytical technologies that may be applied. For complex analytical methods requiring laboratory equipment, ways to enable transportation and storage of samples without interfering with the integrity of analytes must be found.

One way to allow for transportation of body samples is to preserve the cells contained within the samples and thus to enable for cell based cytological or histological examination of the sample material. Examples for preservation solutions for cytological examinations comprise Digene's Universal Collection Medium (WO9931273), Cytyc®'s PreservCyt® Solution (EP0511430), or Surepath® Cytorich® solution. These media are designed to preserve cellular morphology and also the integrity of cellular proteins to allow for cytological examination of the preserved cellular samples. All such preservation solutions comprise alcohols as fixatives. Generally spoken, preservation of the analytes in such procedures is achieved by addition of chemical preservative substances. In cases where the cellular integrity is no longer needed for the diagnostic procedure the integrity of the analytes in a solution may similarly be achieved by addition of chemical preservative substances. The main disadvantage of this approach is that preservatives are often toxic substances that may harm operators and may damage the environment in case of spill. Additionally the requirements for waste disposal as well as the cost for waste disposal are increased when using chemical additives for sample stabilization.

One further approach to solve the problem of stability of analytes in body samples is refrigeration or freezing of the body samples during transportation and storage. It is known that biological substances may be preserved by refrigeration for a certain period of time and that freezing of biological material below $-20°$ C. may be applied for preservation of long term storage. This solution however has the disadvantage of energy consumption and posing hurdles on the transportation process. It cannot always be ensured that refrigeration or maintaining temperatures below $-20°$ C. may be upheld throughout the transportation. This turns out to be a serious problem in cases where the stability of an analyte is not proven under certain temperature conditions. Therefore the method of the present invention involving a heating step provides an easy way to stabilize samples for transportation and storage without the need for addition of preservatives or the need for refrigeration.

Additionally, the heating step if performed in a medium that comprises denaturing agents may contribute to the reproducibility and accuracy of subsequent analytical steps. If the heating step is e.g. performed in the presence of Sodium Dodecyl Sulfate that interacts with proteins in the respective sample, a denatured structure of the proteins is obtained. This denatured structure may in certain cases be of advantage for the reproducible and quantitative determination of the protein in solution.

In the art, methods for denaturing protein bio-assays are used in the case of the Laemmli-System in denaturing Polyacrylamide Gel Electrophoresis in the presence of SDS (known as SDS PAGE). In this case the samples containing proteins are also heated in the presence of SDS to allow denaturation of the protein and are subsequently separated according to their size in an electrophoretic step. The purpose of the denaturation in this method is denaturation of the protein to allow for an overall linearization of the proteins together with homogeneous loading of the proteins with SDS ions. This ensures that proteins in contrast to their native form exhibit an electrical charge that is proportional to the overall size of the molecules. The overall method allows for separation of the molecules by size.

The present invention is based on the inventor's findings that analytes in solubilzed body samples may be stabilized by heating of the sample solution for a certain period of time. According to the present invention heating may for example be performed in a suitable sample medium. The method according to the present invention overcomes the drawbacks of the methods known in the art. The method found by the inventors does not make use of chemical preservatives that may cause harm to animals, human beings or the environment and does not impose the need for refrigeration or keeping up of other energy consuming conditions during the whole process of transportation and storage.

The effect of denaturing of the proteins during the heating step allows for accurate determination of the proteins within the samples using denaturing bioassays. In contrast to the methods known in the art, the denaturing immunoassay is immunochemical detection directly from the sample solution employing a solid phase fixed detection probe that specifically binds to the proteins within the sample. An electrophoretic step is not necessarily comprised in the overall method. The purpose and effect of the denaturation in the context of this method is therefore not due to the generation of homogeneous size dependant electric charge of the proteins but is in part due to the linearization and therefore to improved accessibility of antigenic epitopes within the proteins.

SUMMARY OF THE INVENTION

The present invention is based on the inventors findings illustrated in the following description of the invention and exemplified in the Examples provided herein that analytes in solutions of body samples may be stabilized by a heating step. The heating step comprises the heating of a sample solution preferably in the presence of a denaturing agent for a period of time to a temperature sufficient to allow the sample to be stabilized. The invention furthermore pertains to the improvement of accurate and quantitative or semi-quantitative determination of e.g. protein-analytes in solutions by denaturing the protein contained therein by heating in the presence of a denaturing agent to allow partial denaturation of the protein within the solution and subsequent immuno-chemical quantitative or semi-quantitative determination of the protein. The method is e.g. applicable to preservation of analytes for subsequent assay in the course of assessment or support of diagnosis on the basis analyte levels in said body samples. The method may be applied to any kind of body sample obtained for diagnostic or whatsoever purpose.

One aspect of the present invention is a method for stabilization of analytes in solutions of solubilized body samples. The method comprises the steps of solubilizing the samples material obtained from a subject in a suitable sample medium and stabilizing the sample contained within the sample medium by heating said sample medium for a certain period of time. The method is suited for stabilization of analytes and may especially be applied under circumstances where cooling or refrigeration is not possible and where chemical preservative substances shall or must be avoided.

A second aspect of the present invention is a method for denaturing immunoassay of proteins in solution, wherein at least one step of the immunoassay is carried out in presence of the denaturing agent in a concentration that allows to uphold the denatured status of an analyte protein.

A third aspect of the present invention is a sample comprising analytes suited for biochemical or immunochemical analysis to be used e.g. as a standard or control sample for an assay or assay kit, that has been treated according to the method of the present invention.

A fourth aspect of the present invention is a device for heating samples according to a method of the present invention, the device being characterized in having a timer and drillings suited to fit the sample collection vials.

A fifth aspect of the present invention is a sample collection vial containing a medium comprising agents suited for stabilization and/or denaturation of body samples according to a method of the present invention.

BRIEF DESCRIPTION OF THE DRAWINGS

FIG. 9 shows the p16$^{INK4a}$ ELISA results in the presence of 0.5% SDS and 3% TRITON® X100 (4-(1,1,3,3-tetramethylbutyl)phenyl-polyethylene glycol solution). The p16$^{INK4a}$ levels were measured in an ELISA out of samples containing 3% TRITON® X100 and 0.5% SDS. Samples with cytologically reported abnormality of the epithelium of the uterine cervix were applied. The graph shows the OD measured in the ELISA in correlation to the cytological diagnosis available. For details see Example 1a.

DETAILED DESCRIPTION OF THE INVENTION

Figure 1:
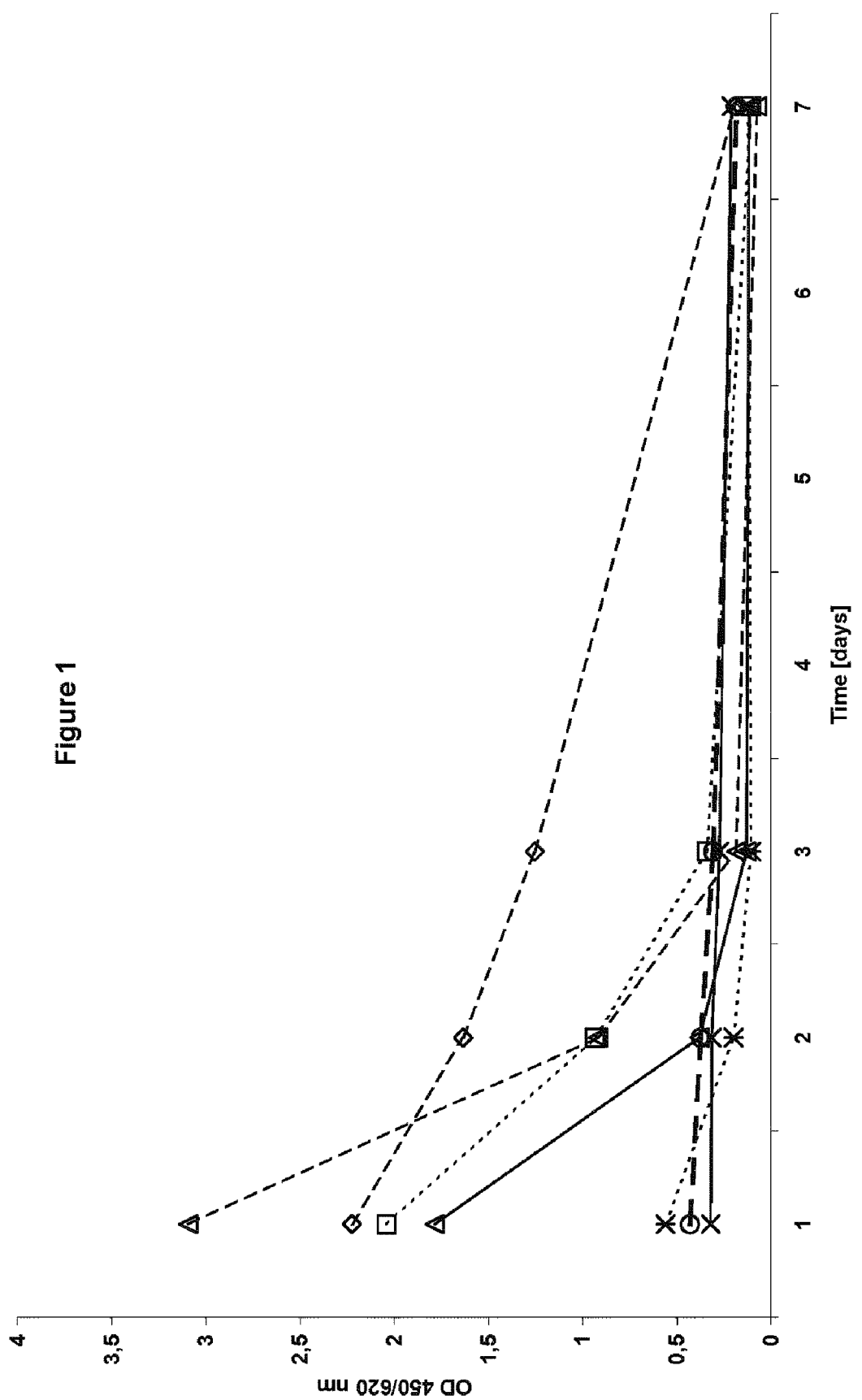
FIG. 1 shows the stability of $p16^{INK4a}$ in solubilized samples. The levels of $p16^{INK4a}$ were determined in samples from the human cervix uteri using an ELISA. The cervical samples were solubilized in a sample medium and thereafter incubated for several days at ambient temperature. Aliquots from each sample were taken for determination of the $p16^{INK4a}$ levels on day 1 (immediately after heat treatment), day 2, day 3 and day 7. The graph shows $p16^{INK4a}$ levels determined in 7 samples at different points in time and thus displays instability of $p16^{INK4a}$ within the particular patient samples under the given conditions. For details see Example 1.

Based on the findings of the inventors stabilization of analytes in body samples may be achieved by solubilizing said body samples in a suitable sample medium and subsequently subjecting the solubilized samples to a heating step before transportation and storage of the samples. Furthermore the step of heating of the samples in the presence of denaturing agents may contribute to the accurate quantitative determination of analytes in the samples.

Medical examination procedures are commonly accompanied or supported by the assay of analytes within body samples. Such analytes may e.g. be assayed in clinical chemistry laboratory procedures.

The expression analyte as used in the context of the present invention shall refer to molecules that may be detected in the course of an analytical testing procedure. In certain embodiments of the present invention the analytes are e.g. nucleic acid as well as (poly)peptide molecules. Such analytes thus comprise e.g. RNA (mRNA, hnRNA, etc.), DNA (cDNA, genomic DNA, etc.), proteins, polypeptides, proteoglycans, glycoproteins and the respective fragments of these molecules.

Analytes may be whatsoever molecules. In certain embodiments of the present invention analytes are molecules with a special relevance for the detection of diseases in mammalians. Diseases according to the present invention may comprise any kind of medically relevant conditions comprising but not limited to neoplastic, inflammatory, infectious, degenerative, genetic, proliferative and vascular diseases as well as premalignant and malignant cancerous conditions. In certain embodiments of the invention premalignant and malignant cancerous conditions may comprise neoplastic disorders such as tumors. Tumors may comprise tumors of the head and the neck, tumors of the respiratory tract, tumors of the anogenital tract, tumors of the gastrointestinal tract, tumors of the urinary system, tumors of the reproductive system, tumors of the endocrine system, tumors of the central and peripheral nervous system, tumors of the skin and its appendages, tumors of the soft tissues and bones, tumors of the lymphopoietic and hematopoietic system, etc. Tumors may comprise for example neoplasms such as benign and malignant tumors, carcinomas, sarcomas, leukemias, lymphomas or dysplasias. In a particular embodiment, the tumor is for example cancer of the head and the neck, cancer of the respiratory tract, cancer of the anogenital tract, cancer of the gastrointestinal tract, cancer of the skin and its appendages, cancer of the central and peripheral nervous system, cancer of the urinary system, cancer of the reproductive system, cancer of the endocrine system, cancer of the soft tissues and bone, cancer of the hematopoietic and lymphopoietic system.

Tumors of the anogenital tract may comprise cancer of the perineal and the scrotal skin, cervical cancer, cancer of the vulva, cancer of the vagina, cancer of the penis, cancer of the anus, etc. Cervical cancer may comprise squamous lesions, glandular lesions or other epithelial tumors. Squamous lesions comprise, e.g., cervical intraepithelial neoplasias (mild, moderate and severe dysplasia), carcinoma in-situ, squamous cell carcinoma (e.g., keratinizing, nonkeratinizing, verrucous, warty, papillary, lymphoepithelioma-like). Glandular lesions may comprise atypical hyperplasias, adenocarcinoma in-situ, adenocarcinoma (such as, e.g., mucinous, endometrioid, clear cell, adenoma malignum, papillary, serous or mesonephric adenocarcinoma). Other epithelial tumors may comprise adenosquamous carcinoma, glassy cell carcinoma, adenoid cystic carcinoma, adenoid basal carcinoma, carcinoid tumor, small cell carcinoma and undifferentiated carcinoma. For more detailed information, confer "Kurman, R., Norris, H., et al., Tumors of the Cervix, Vagina, and Vulva, Atlas of Tumor Pathology, 1992, AFIP," the contents of which shall be incorporated herein by reference.

Gastrointestinal tumors may comprise colon cancer, cancer of the colon ascendens, of the colon descendens, of the colon transversum, of the sigmoidum, of the rectum, cancer of the small intestine, cancer of the jejunum, cancer of the duodenum, gastric cancer, oesophageal cancer, liver cancer, cancer of the bile, cancer of the biliary system, pancreatic cancer, etc. A comprehensive overview over gastrointestinal lesions is given in "Hamilton Sr, Aaltonen L A (Eds.): World Health Organization Classification of Tumours, Pathology and Genetics of Tumors of the Digestive System, IARC Press: Lyon 2000," which shall be incorporated herein by reference.

Tumors of the respiratory tract may comprise any malignant condition of the respiratory tract such as, e.g., cancer of the lung, the alveoles, the bronchioles, the bronchial tree and the broncus, the nasopharyngeal space, the oral cavity, the pharynx, the nasal cavity and the paranasal sinus. Lung cancer such as small cell lung cancer, non-small cell lung cancer, squamous cell lung carcinoma, small cell lung carcinoma, adenocarcinoma of the lung, large cell lung carcinoma, adeno-squamous lung carcinoma, carcinoid tumor of the lung, bronchial gland tumor or (malignant) mesothelioma. An overview over tumors of the respiratory tract may be found in Colby T V, et al.: Tumors of the Lower Respiratory Tract, Atlas of Tumor Pathology, Third Series, Fascicle 13, AFIP: Washington 1995," which shall be incorporated herein by reference.

Tumors of the urinary system may comprise bladder cancer, cancer of the kidney, renal pelvis, cancer of the ureters and cancer of the urethra, etc. Tumors of the reproductive system may comprise cancer and precursory stages thereof of the ovary, the uterus, the testis, the prostate, the epididymis, etc.

Molecules with a special relevance for disease that may be used as analytes according to the present invention may be molecules that may be used for detection of the presence or absence of such disease. The molecules may be indicative of the presence or absence of the disease in various ways. Such ways may comprise altered expression levels (e.g. increased, decreased, temporally or locally altered) as well as expression of molecules with altered characteristics. Such altered characteristics may comprise any kind of modified molecules. Such modifications comprise modifications of the sequence of molecules (such as mutations, deletions insertions, etc.) as well as any other type of modifications of the molecules (such as e.g. chemical modifications, phosphorylations, glycosylations, derivatization, dephosphorylation etc.).

In certain embodiments of the present invention the analytes may e.g. be cancer marker molecules or tumor markers. The analytes may be selected from a group comprising markers for cell proliferation, markers characteristic for apoptosis, markers for cell surface epitopes, markers associated with viral infection or viral activity in cells (e.g. markers for infection by high risk human papilloma virus selected from a group comprising HPV16, HPV18, HPV31, HPV 33, HPV35, HPV 39, HPV 45, HPV 51, HPV 52, HPV56, HPV 58, HPV 59, HPV 66 and HPV 68), markers characteristic for cell differentiation etc. In certain preferred embodiments the analytes are cyclin dependent kinase inhibitors.

Analytes may e.g. comprise molecules derived from proteins selected from a group comprising p13.5, p14, p15, p16 (also referred to p16$^{INK4a}$), p19, p21, p27, p53, pRb, p14ARF, cyclin A, cyclin B, cyclin E, MDM-2, CDC2, Id1, osteopontine, GRP, renal dipeptidase, her2/neu, TGFβII receptor, Cytokeratines, (e.g. cytokeratin 8, cytokeratin 10, cytokeratin 18), mucin antigens (MUC1, MUC2, Tn, STn), EpCAM and gCatenin, concanavalin A receptor, GalNacTransferase, oligosaccharyltransferase, lectins (ConA, WGA, PNA, UEA I, DBA, SBA, SNA), plakophilin, vimentin, CD antigens (e.g. CD3, CD16, CD18, CD4, CD8, CD56, CD19, CD20), HPV associated markers e.g. derived from HPV genes L1, L2, E1, E2, E4, E5, E6 or E7, CDC6, MCM2, MCM3, MCM4, MCM5, MCM6, MCM7, CDC7 protein kinase, Dbf4, CDC14 protein phosphatase, CDC45 and MCM10, Ki67, Ki-S2, PCNA, a helicase, a topoisomerase, Topo2alpha, transcription factors, members of the E2F-family, Brn-3a, Brn-3b or POLD etc.

Analytes may be molecules that are detected on a qualitative, semiquantitative as well as a quantitative basis. A quantitative value may e.g. be represented in terms of a concentration. A semiquantitative value may be expressed in terms of a scale of levels e.g. undetectable levels, low levels, intermediate levels, high levels or any other suitable mode. The level of an analyte may also be represented in terms of a dependent parameter such as the intensity of a signal generated in an assay format in response to the presence of a marker molecule. For the expression of the signal intensity in semi-quantitative as well as in quantitative assays relative units may be used for the expression of the determined amounts of analyte. The relative units used may be denominated in any suitable manner such as e.g. as units per mL of sample (U/mL). Such units may be directly related to real molar concentration of analytes as measured in a solution but may also be arbitrary units as applicable for the respective assay format.

Analytes are detected by immunoassay according to the present invention. Immunoassay according to the present invention is any immunochemical detection of an analyte. Such immunochemical detection may in certain embodiments comprise assays where one or more probes or antibodies are used for capture of the analyte molecules and subsequent detection of the analyte probe/antibody complex. Such reaction may either be performed in solution or fixed to a solid phase. Those of skill in the art know appropriate immunoassays. Such assay may comprise ELISA and various kind of other immunoassays. Such immunoassays may comprise but not be limited to for example immunoprecipitation or immunological assays, such as EIA, ELISA, RIA, ECLIA, LIA, lateral flow assays, flow through assays, immunochromatographic strips, etc. Immunoassays for use in the invention may comprise competitive as well as non-competitive immunoassays. In certain embodiments antibodies or probes fixed to solid phases may be employed in the immunoassays. Solid phases may comprise various embodiments of solid substances such as planar surfaces, particles (including micro-, nano-particles or even smaller particles). In certain embodiments, particles may be provided as spheres, beads, colloids, or the like.

The fixation of reagents to the solid phase in a test kit or an in-vitro diagnostic device may be carried out via direct fixation or via indirect fixation. Direct fixation may be carried out by covalent binding, non-covalent binding, association, or adsorption to surfaces. Indirect fixation may be carried out through binding of the antibody to agents which themselves are directly fixed to solid phases. Binding agents include avidin, streptavidin, biotin, digoxigenin, antibodies or the like.

The immunoassay may comprise one or more further reactions with detecting agents either recognizing the analytes or preferably recognizing probes used to recognize the analytes. The detection reaction further may comprise a reporter reaction indicating the level of the analytes.

Detection systems may be e.g. chromogenic systems, luminescence systems (electroluminescence, bioluminescence, photoluminescence, radioluminescence, chemiluminescence, electrochemiluminescence), fluorescence based systems, conductivity based detection systems, radiation (light, UV, X-ray, gamma etc.), plasmon resonance (e.g. Surface Plasmon Resonance SPR) or any other known method.

According to the present invention the body sample solubilized within the sample medium may directly be applied as specimen for the performance of the immunoassay. In certain embodiments of the present invention high concentrations of detergents may be present during immunoassay. The immunoassay may therefore in certain embodiments of the present invention be an immunoassay that is especially tolerant against denaturing conditions. In certain embodiments of the invention the immunoassays are tolerant against concentrations of SDS above 0.1%, in a preferred embodiment the immunoassays are tolerant against SDS concentrations above 0.3%. In another preferred embodiment the immunoassays are tolerant against concentrations of SDS above 1%.

The detection of analytes is commonly performed using one or more "probes" (used interchangeably with the term "binding agents" within the present invention) for the detection of the analyte. The probe may for example be an antibody specifically binding to the analyte. The term "antibody" in all its grammatical forms shall in the context of the present invention refer generally to antigen binding molecules including but not limited to monoclonal and polyclonal antibodies, fragments of antibodies, antigen binding epitopes, mini-antibodies, peptidomimetics with antigen-binding properties, anticalines and diabodies. Generally the detection of the analyte shall comprise detection of the presence or absence and or the level of analytes.

The expression "body sample" as used herein comprises any body samples of any kind and nature. Examples of such body samples are secretions, swabs, lavages, body fluids, semen, cell- and tissue-samples, blood, smears, sputum, urine, stool, liquor cerebrospinalis (short denominated as "liquor" herein), bile, gastrointestinal secretions, lymph, bone marrow, aspirates and biopsies of organs such as needle or punch biopsies and (fine)-needle aspirates. In particular, smears, swabs and biopsies are indicated when the detection of anogenital cancers, e.g. cervical cancers, is concerned. The term biopsies as used throughout this text shall comprise all kind of biopsies known to those of skill in the art. Thus biopsies as used in the context of the present invention may comprise e.g. resection samples of tumors, tissue samples prepared by endoscopic means or punch- or needle-biopsies of organs. Biopsies comprises specimens obtained by several different methods such as cold knife biopsies, LEEP (loop electrocautery excisional procedure) biopsies, etc. Body samples according to the present invention may in certain embodiments of the invention refer to specimens comprising cellular material obtained from the human body. Such samples may e.g. comprise specimens that are suited for use in cytological examination. Examples are swab samples, liquid based cytology samples and smears.

Liquid based cytology samples may comprise any kind of liquid based cytology sample comprising e.g. cell or tissue samples preserved in any standard sample collection, storage or transportation medium, known to those of skill in the art such as e.g. commercially available preservation media (formalin solution, Cytyc "PreservCyt" or "CytoLyt", Digene "Universal Collection Medium", Tripath Imaging "Cytorich", etc.). Alternatively cell preservation media for liquid based cytology samples may contain a mixture of one or more selected from a group comprising alcohols, aldehydes, ketones, acids, metal-ions or sublimates, ethers etc. for preservation of cellular components.

Alcohols include methanol, ethanol, (n- or i-) propanol, (n-, i- or t-) butanol or higher branched or unbranched alcohols. Aldehydes include formaldehyde, acetaldehyde, glutaraldehyde, etc. Ketones such as Acetone may be used. Acids for use in standard sample media include organic acids (acetic acid, trichloro-acetic acid, salicylic acid, picric acid) or inorganic acids such as e.g. chromic acid. Standard sample solutions may comprise metals such as silver, copper, chromium, mercury, osmium, uranium. Solutions of salts such as uranylacetate, potassiumbichromate, ammonium sulfate, etc. may be components of preservative media. In preferred embodiments the Liquid based cytology specimens are especially suited for subsequent immunochemical detection of protein analytes in the samples.

In certain embodiments of the present invention the body sample may be obtained from a device that is used for obtaining a specimen for testing in another procedure before such device is discarded. Devices may for example comprise any kind of brush, broom, spatula, swab, etc. Such devices comprise e.g. swabs made from Dacron®, cotton or any other suitable fiber, brushes such as Endocervical brush, Medscand system for cervical sampling, CERVEXBRUSH®, CERVEXBRUSH COMBI™ from Rovers Medical Systems, N.V., CYTOBRUSH® from Medscand Medical AB and Digene Corp.'s CERVICAL CELL SAMPLER™.

In certain embodiments the body sample according to the present invention is obtained from the devices after sample material for another testing procedure has been obtained. For example the sampling device may be used for preparation of a conventional smear sample and may thereafter be contacted to a sample medium according to the present invention. Alternatively the sampling device may also be used for preparation of any kind of liquid based cytology sample and be contacted to the sample medium according to the present invention subsequently. In the case of liquid based cytology samples it is also intended by the inventors that part of the liquid based cytology sample may be used to be contacted with the sample medium and be solubilized for stabilization or analysis by a denaturing immunoassay.

Contacting of the sampling device to a sampling medium may comprise immersing the sampling device into a vial containing the sample medium. In certain embodiments the sampling device is immersed in the medium to fully cover the part of the sampling device that has been contacted to the human body with the sample medium. Upon immersing the sampling device into the sample medium the device may be swirled in the medium. Alternatively the medium together with sampling device may be shaken or vortexed. In certain cases the sampling device may be contacted to the sample medium in a way that the device or part of the device is stored or left within the sample medium for a period of time to allow complete dissolution of the cells or cell debris. In certain cased the sampling device may e.g. be heated together within the sample medium.

Generally the performance of an immunoassay may take place immediately after the body sample has been contacted with the sample medium or may take place after a certain period of time. In certain embodiments of the invention the immunoassay is performed directly when the lysis of the body sample is completed or is believed to be completed. In certain further embodiments of the invention after completion of the lysis of the body sample the sample solution is stored for a period of time that may range between minutes up to weeks. In one preferred embodiment the time between lysis of the body sample in the sample medium and the performance of the immunoassay is a period of time not shorter than 1 Minute and not longer than 90 days, in an even more preferred embodiment the period of time is not shorter than 1 hour and not longer than 14 days and in another preferred embodiment the period of time is not longer than 7 days. In certain embodiments the time period may even be up to the range of years.

Body samples according to the present invention may be contacted to a sample medium immediately after obtaining the samples or even after a certain span of time has passed by. During this time the body samples may e.g. be refrigerated, frozen or preserved in a cell preservative solution. The methods for such cell preservation or for preservation by freezing or refrigeration are known to those of skill in the art.

According to the present invention one body sample may be used for the detection of one or more analytes in immunochemical analysis. The detection of the analytes may be performed in one single assay or in multiple distinct assays. In certain embodiments of the invention accordingly only an aliquot of a total body sample is employed for the determination of a single analyte out of the body sample.

The terms "solubilized" or "solubilization" as used in the context of the present invention shall mean that the components of a body sample are contacted to a sample medium and are at least in part dissolved in the sample medium and subsequently the components of the body sample are at least in part represented by the components of the solution.

The term "sample medium" as used in the context of the present invention may be any liquid known to those of skill in the art to be suited for solubilization of cellular components or of whole cells. The sample medium may, for example, be organic or aqueous solutions of chaotropic agents such as e.g. urea, GuaSCN, formamide, of detergents such as anionic detergents (e.g. SDS, N-lauryl sarcosine, sodium deoxycholate, alkyl-aryl sulfonates, long chain (fatty) alcohol sulfates, olefine sulfates and sulfonates, alpha olefine sulfates and sulfonates, sulfated monoglycerides, sulfated ethers, sulphosuccinates, alkane sulfonates, phosphate esters, alkyl isethionates, sucrose esters), cationic detergents (e.g. cetyl trimethylammonium chloride), non-ionic detergents (e.g. TWEEN® 20 (polyoxyethylene-sorbitan monolaurate), Nonidet P-40 (nonylphenylpolyethylene glycol), TRITON® X-100 (4-(1,1,3,3-tetramethylbutyl)phenylpolyethylene glycol solution), Igepal CA-630 (octylphenoxy)polyethoxyethanol), N-octyl-Glucosid) or amphoteric detergents (e.g CHAPS (3-[(3-cholamidopropyl)dimethylammonio]-1-propanesulfonate), 3-dodecyl-dimethylammonio-propane-1-sulfonate, lauryldimethylamine oxide) and/or of alkali hydroxides such as e.g. NaOH or KOH. In certain embodiments the sample medium may also comprise inorganic or organic acids as components such as formic acid, acetic acid, phosphoric acid etc. In certain embodiments, where lysis of cells may be achieved without the use of detergents, hyper- or hypotonic solutions or buffers or simply water or an organic liquid may be used as solvent. Any liquid that is suited to solubilize the cellular components of body samples in total or in parts may be regarded as a sample medium as used herein. Thus sample media as used herein may but need not contain buffer substances or have buffer capacity.

Generally any suitable liquid may be used in the sample medium of the present invention. The liquid may be organic or inorganic and may be a pure liquid, a mixture of liquids or a solution of substances in the liquid and may contain additional substances to enhance the properties of the solvent. In certain embodiments, where lysis of cells may be achieved without the use of detergents, hyper- or hypotonic solutions or buffers or simply water or an organic liquid may be used as solvent. Any liquid, that is suited to solubilize the cellular components of body samples in total or in parts may be regarded as a sample medium as used herein. Thus sample media as used herein need not contain buffer substances or have buffer capacity. However in certain embodiments of the invention the sample media may have buffer capacity and may contain buffer substances.

In one embodiment, the sample medium is designed, so that cells, cell debris, nucleic acids, polypeptides, lipids and other biomolecules potentially present in the raw sample are solubilized. In further embodiments of the present invention, the solvent may be designed to assure differential solubilization of specific components of the body sample, leaving other components unsolubilized.

The sample medium for solubilizing the body sample according to the present invention may furthermore comprise one or more agents that prevent the degradation of components within the raw samples. Such components may for example comprise enzyme inhibitors such as proteinase inhibitors, RNAse inhibitors, DNAse inhibitors, etc. In one embodiment of the present invention, the sample is lysed directly in the form obtained from test-individuals. Proteinase inhibitors may e.g. comprise inhibitors of serine proteinases, inhibitors of cysteine proteinases, inhibitors of aspartic proteinases, inhibitors of metallo proteinases, inhibitors of acidic proteinases, inhibitors of alkaline proteinases or inhibitors of neutral proteinases. In certain embodiments of the present invention the inhibition of enzymes may be achieved by chemical means such as e.g. denaturation of the enzymes by means of salt concentration, pH, chaotropic agents or the like.

In certain embodiments of the invention in order to obtain optimal results of the assay, the pH of a sample medium that can be directly applied to the assay system is around neutral. In further embodiments the pH of the sample medium is within the range of 4 to 10. In certain other embodiments, the pH is in a range from 5 to 9. In a preferred embodiment, the pH is in a range from 6 to 8. In a more preferred embodiment, the pH is in the range from 6.5 to 7.5.

Examples of denaturing agents for sample media and/or for denaturing of analytes according to the present invention may for example be selected from the substances given in Table 1.

TABLE 1

| Sample medium |
| --- |
| Detergents: |
| 0.1-1% SDS |
| 0.2-3% SDS |
| 0.2-3% DOC |
| 0.1-1% n-Octylglycoside |
| 0.1-3% TRITON ® x-100% |
| 0.1-1% Chaps |
| 0.1-3% TWEEN ® |
| Detergent-Mix: |
| RIPA (1% NP40, 0.5% DOC, 0.1% SDS, PBS) 40-100% |
| SOX (0.5% DOC, 0.5% n-Octylglycoside) 40-100% |
| Special sample medium (3% TRITON ® X-100, 0.4% SDS, PBS) |
| Commercial lysis media: |
| Dynal (Dynal, Oslo, Norway) |
| M-PER/B-PER (Pierce, Rockford, IL) |
| Miscellaneous: |
| 0.5-8M Urea |
| 1-99% Formamide |
| GuaSCN |
| 1-80% Formic Acid |
| 1-70% Acetic Acid |
| 1-50% Phosphoric acid |
| Laemmli sample buffer (10-80% DMSO, 10-80% Formamide, 50-70% formic acid, PBS, Citrate buffer pH 6.0, 500 mM NaCl in Phosphate buffer) |

All concentrations given in percent (%) throughout the whole disclosure of this invention refer to percent weight per volume (% w/v).

The sample media according to the present invention comprise in preferred embodiments a denaturing agent. Such denaturing agent may be selected from a group comprising detergents or chaotropic agents.

In certain situations, the analytes may be degraded in the solubilized samples and may thus not be detected. This is particularly true, if the samples are directly transferred to a lysing medium and stored therein for a certain period of time before further preparation. To prevent degradation, sample medium may furthermore comprise one or more agents that prevent the degradation of components within the raw samples. Such components may for example comprise enzyme inhibitors such as proteinase inhibitors, RNAse inhibitors, DNAse inhibitors, etc. The inhibitors may e.g. comprise proteinase inhibitors selected from the compositions given in Table 2.

TABLE 2

| Inhibitor | class of inhibited proteinase |
| --- | --- |
| Aprotinin | Serine |
| Benzamidine | Serine |

TABLE 2-continued

| Inhibitor | class of inhibited proteinase |
|---|---|
| Bestatin | Aminopeptidases |
| Calpeptin | Cysteine |
| Cystatin | Cysteine |
| E-64 | Cysteine |
| EDTA | Metallo |
| Elastatinal | Serine |
| EST | Cysteine |
| Fetal calf serum | all classes |
| Leupeptin | Serine/Cysteine |
| a2-Macroglobulin | all classes |
| NCO-700 | Cysteine |
| Pefabloc = AEBSF | Serine |
| Pepstatin A | Aspartic |
| PMSF | Serine |
| o-Phenanthroline | Metallo |

For stabilization purpose, the sample medium may also comprise bulk protein (e.g. albumin such as bovine serum albumin or calf serum albumin, soy lecithin or other bulk proteins) to compete in degradation with the sample proteins. The bulk proteins may e.g. be present in combination with proteinase inhibitors or may be added instead of proteinase inhibitors. In certain embodiments the sample medium may be selected to be compatible with the assay (e.g. ELISA) performance, so that solubilized samples may directly be applied to the assay.

In certain embodiments the sample medium may also comprise substances for inhibition of microbial activity. Such substances may e.g. comprise microbizidic or microbiostatic substances. Such substances comprise e.g. sodium azide, proclin, 5-Bromo-5-Nitro-1,3-Dioxane, 2-Methyl-4-Isothiazolin-3-One, 5-Chloro-2-Methyl-4-Isothiazolin-3-One and mercury containing compounds (e.g. thimerosal).

For overall stabilization of the analytes in the sample medium according to the present invention a heating step is applied.

A sample medium according to the present invention may in certain embodiments also comprise one or more denaturing agents. Such combinations may comprise the denaturing agents as disclosed herein in any suitable combination.

Heating as used in the context of the present invention shall refer to a process of subjecting the sample medium containing the solubilized body sample to temperatures elevated relative to ambient temperature and may pertain to heating to any temperature below at or above the boiling point of a particular sample medium. Heating may e.g. comprise subjecting to temperatures of 30 to 150° C. In certain embodiments heating comprises subjecting to temperatures above 50° C. In a preferred embodiment of the invention heating shall refer to subjecting to temperatures between 70° C. and 130° C. In another preferred embodiment heating comprises subjecting to temperatures between 95 and 110° C.

In the context of the present invention heating is performed for a period of time that allows the analytes contained in the body sample to be optimally stabilized in the sample medium. The period of time required for this may vary and is dependent on the type of samples. In general, the period of time is at least 3 minutes. The heating times (effective incubation times) at a given temperature may be chosen to be between 5 and 30 minutes. In a preferred embodiment of the invention the incubation time is between 10 and 27 minutes. In another preferred embodiment the incubation time is between 15 and 25 minutes. The overall heating time at a given temperature must be differentiated from the time for incubation of the sample solution at a given temperature. The heating time (effective incubation time) given above shall refer to the time the sample solution is heated in a heating device comprising the time period during which the temperature of the sample solution is equilibrated to the final incubation temperature. This is generally longer than the period of time for incubation at the envisaged incubation temperature after the sample solution has been equilibrated to the incubation temperature. For mere incubation at the destined temperature a period of time from 1 minute to 30 minutes may be regarded suitable for the methods according to the present invention. In a preferred embodiment of the present invention a period of time of 3 to 15 minutes is used for heating. In certain embodiments of the invention periods of time between 5 and 12 Minutes are sufficient. The incubation times given are strongly dependent on the heating device used as well as on the vial type and on the sample media used. Therefore the time period needed for incubation may exceed or even be shorter than the time period given above. Those of skill in the art know how to determine the period of time necessary for incubation of an ambient temperature equilibrated sample solution that has been introduced into an already hot heating device to allow for an incubation of the sample solution at the envisaged incubation temperature for the planned period of time. Heating devices for performing the method of the present invention can be any heating device applicable for heating a sample solution in a laboratory for a fixed period of time. Generally heating devices are equipped with a thermostat and may be set to hold a fixed pre-selected temperature. Such heating devices may e.g. comprise water baths, microwave ovens and heating blocks. In certain embodiments of the invention the heating device is equipped with a timer that allows the user to control the incubation time easily. Otherwise the user may use an external timer (such as e.g. an alarm clock) to control the incubation time.

Stabilization as used in the context of the present invention shall refer to a situation where an analyte that is incubated within the sample medium at a certain temperature degraded or otherwise modified thus rendering the analyte undetectable or detectable at an altered level compared to the starting point of the incubation after a certain period of time. The stabilization shall in certain embodiments of the invention refer to a stabilization of the detectable level of analytes within the sample solution. In certain embodiments a deviation of the level of analyte detectable after a certain period of time of 30% or less compared to the level detectable at the beginning of the time period, is regarded as stable. In certain preferred embodiments a deviation of 20% or less is regarded as stable. In certain especially preferred embodiments a deviation of 15% or less is regarded as stabilization of the analyte.

In certain embodiments of the present invention the stabilization is especially stabilization for storage and transport of the samples at ambient temperature. Ambient temperature shall confer mainly to temperature between −20° C. and +50° C. Stabilization in special embodiments of the present invention may also refer to stabilization of the analyte at special temperature ranges and may also refer to stabilization for storage and transport condition between 2° C. and 30° C. In yet another embodiment the temperature range may be between −80° C. and 20° C. In certain embodiments the stabilization shall especially refer to a state, where the temperature of the samples is not controlled at all, so that any temperature present in the transport or storage environment may be accepted for the sample and stability in the sense of no alteration of the level of the analyte detectable by a certain detection method takes place. In some embodiments of the present invention the stabilization of the analyte may also be achieved for any temperature of storage and transport.

Denaturing an analyte or denaturation of an analyte as used in the context of the present invention shall refer to any kind of altering the analyte or alteration of the analyte respective the native state thereof. In certain embodiments of the invention such alteration respective the native state may comprise any kind of disruption of the native or naturally occurring secondary, tertiary or quaternary structure of an analyte (protein).

One aspect of the present invention pertains to a denaturing bioassay. A denaturing bioassay in the context of the present invention is an immunochemical assay that is designed to detect the presence or absence and or the level of an analyte within a sample solution. Such bioassay is preferably an assay where the detection of the analyte is carried out in a liquid phase or using reagents fixed to a solid phase. In any case a denaturing bioassay according to the present invention is characterized in at least one step of the immunochemical reaction being carried out in the presence of denaturing agents. In contrast to the situation in a denaturing bioassay according to the present invention, in SDS-PAGE only the gel electrophoresis is carried out under denaturing conditions and the subsequent immunochemical detection reaction is carried out, after the denaturing agents have been washed away. An example of a denaturing bioassay according to the present invention is e.g. a sandwich ELISA where the antigen capturing step is carried out directly from the sample solution containing the analyte and the denaturing agent. In such case the sample solution comprising a denaturing agent is contacted to a solid phase fixed antibody directed against a particular analyte. The capture of the analyte by the capture antibody is performed and the denaturing agent is washed away only after that step. The advantage of such method is, that conformational changes present in the denatured analyte are upheld during the capture step and thus interaction of the probe or antibody may take place with the denatured analyte. This may in certain cases lead to improved accuracy in detection of the analyte. Especially where linear epitopes of an analyte have been employed for generation of probes or antibodies the detection of such analytes by said antibodies may be improved if the immunochemical reaction is carried out under denaturing conditions.

In the art however there was the prejudice that high concentration of denaturing agents interfere with the immunochemical reaction and thus antigen binding cannot take place in a proper way if there is e.g. SDS present in the incubation solution. The inventors now found that such elevated concentrations of denaturing agents may be of positive impact on the performance of an immunochemical detection reaction under certain circumstances as described above.

The present invention provides a method for detecting one or more analyte proteins by an immunoassay, comprising the step of carrying out an immunoassay in the presence of one or more denaturing agents in a concentration to allow to uphold the denatured status of the one or more analyte proteins. For example, the method comprises the steps of i) bringing a sample comprising the one or more analyte proteins into contact with the one or more denaturing agents, ii) heating said sample for at least 3 minutes in the presence of the one or more denaturing agents to allow the protein to be denatured and iii) performing one or more immunoassays for detection of the one or more analyte proteins using the sample of (ii) as a specimen for the test.

Denaturing immunoassays according to the present invention may comprise but not be limited to for example immunoprecipitation or immunological assays, such as EIA, ELISA, RIA, ECLIA, LIA, lateral flow assays, flow through assays, immunochromatographic strips, latex agglutination assays etc. Immunoassays for use as denaturing immunoassays in the invention may comprise competitive as well as non-competitive immunoassays. In certain embodiments antibodies or probes fixed to solid phases may be employed in the immunoassays. Solid phases may comprise various embodiments of solid substances such as planar surfaces, particles (including micro-, nano-particles or even smaller particles). In certain embodiments, particles may be provided as spheres, beads, colloids, or the like.

The fixation of reagents to the solid phase in a test kit or an in-vitro diagnostic device may be carried out via direct fixation or via indirect fixation. Direct fixation may be carried out by covalent binding, non-covalent binding, association, or adsorption to surfaces. Indirect fixation may be carried out through binding of the antibody to agents which themselves are directly fixed to solid phases. Binding agents, for example, include avidin, streptavidin, biotin, digioxingenin, antibodies or the like.

The immunoassay may comprise one or more further reactions with detecting agents either recognizing the analytes or preferably recognizing probes used to recognize the analytes. The detection reaction further may comprise a reporter reaction indicating the level of the analytes.

Detection systems may be e.g. chromogenic systems, luminescence systems (electroluminescence, bioluminescence, photoluminescence, radioluminescence, chemiluminescence, electrochemiluminescence), fluorescence based systems, conductivity based detection systems, radiation (light, UV, X-ray, gamma etc.), plasmon resonance (e.g. Surface Plasmon Resonance SPR) or any other known method.

The denaturing agents used for such denaturing bioassay may in certain embodiments of the invention be part of the sample medium into which body sample are introduced for storage and transport before analysis. In other embodiments the denaturing agent is contacted to the analyte proteins in a sample just before the step of denaturation. Denaturing agents used for the denaturing bioassay as disclosed herein may for example comprise chaotropic agents such as e.g. urea, GuaSCN, formamide, detergents such as anionic detergents (e.g. SDS, N-lauryl sarcosine, sodium deoxycholate, alkylaryl sulfonates, long chain (fatty) alcohol sulfates, olefine sulfates and sulfonates, alpha olefine sulfates and sulfonates, sulfated monoglycerides, sulfated ethers, sulphosuccinates, alkane sulfonates, phosphate esters, alkyl isethionates, sucrose esters), cationic detergents (e.g. cetyl trimethylammonium chloride), non-ionic detergents (e.g. TWEEN® 20, Nonidet P-40, TRITON® X-100, NP-40, Igepal CA-630, N-Octyl-Glucosid) or amphoteric detergents (e.g CHAPS, 3-Dodecyl-dimethylammonio-propane-1-sulfonate, Lauryldimethylamine oxide) and alkali hydroxides such as e.g. NaOH or KOH. In certain embodiments the denaturing agents may also comprise inorganic or organic acids as components such as formic acid, acetic acid, phosphoric acid etc.

According to the present invention elevated concentrations of detergents may be present during immunoassay. In certain embodiments of the invention the immunoassays are tolerant against concentrations of SDS above 0.1%, in a preferred embodiment the immunoassays are tolerant against SDS concentrations above 0.3%. In another preferred embodiment the immunoassays are tolerant against concentrations of SDS above 1%. In certain embodiments of the invention the immunoassay may be tolerant against concentration of TRITON® X 100 from below 0.1% up to at least 3%.

A further aspect of the present invention is an automated heating device comprising a timer that is designed to perform a heating cycle for a method according to the present invention. The heating device is designed to bring samples solubilized in a sample medium to a target temperature and to maintain the samples at the target temperature for a certain amount of time.

In the most preferred embodiment of the invention automated shall mean that the temperature setting is preset within the device and the user cannot and need not set the temperature for incubation. Furthermore automated shall mean that also the time for incubation is preset in the device. The user may only start the preset incubation cycle without being in the position to influence the preset parameters. Such automation is suited to reduce errors respective the incubation parameters.

In certain embodiments the heating device is designed to bring the samples to and to maintain the temperature within said samples at a temperature of 70° C. or higher. In further embodiments the heating device is designed to bring the samples to and to maintain the temperature within said samples at a temperature of 90° C. to 110° C. In the most preferred embodiment the heating device is designed to bring the samples to and to maintain the temperature within said samples at a temperature of 95° C. to 99° C. Due to measuring artefacts and/or measuring imprecision the temperatures given are to be understood as +/−2° C.

The heating device is designed to maintain the temperature within the sample for a time of at least 5 minutes. In another embodiment the heating device is designed to maintain said temperature within the sample for 7 to 30 Minutes. In the most preferred embodiment the heating device is designed to maintain the temperature within the sample for a period of time of 10 minutes to 27 minutes.

In certain embodiments the heating device may be automated in a way to allow automatic detection of the end of the incubation period with automatic shut off of the device. In further embodiment the device may be equipped to give an acoustic, vibration or optic signal at the end of the incubation period.

In a preferred embodiment the heating device may be a heating block with drills that may take up sample vials.

The examples provided below are indicated for illustration of the subject matter of the invention and are not intended to limit the scope of the invention. Several variations to the examples as provided may be performed by those of skill in the art. The examples therefore provide only a limited scope of embodiments of performance of the methods under the presently detailed invention. Based on the comprehensive testing performed by the inventors, we believe that the methods disclosed is easily transferable to other analytes and other denaturing agents without altering the positive effects of the inventive methods as detailed herein.

EXAMPLES

Example 1

Stabilization of $p16^{INK4a}$, Ep-Cam and Gamma Catenin Proteins in Samples from the Uterine Cervix The levels of $p16^{INK4a}$ protein were determined in cervical specimens obtained with a standard cervical sampling device. 11 samples were subjected to a heating step according to the invention disclosed herein, and were analysed for the level of $p16^{INK4a}$ after storage for a certain period of time thereafter; further 7 samples were directly used for analysis of the samples for the level of $p16^{INK4a}$ protein by ELISA technique.

Sample Preparation and Stabilization

For the present examples patient sample were collected by gynecologists using an endocervical brush or a CERVEX-BRUSH COMBI® (Rovers Medical Devices). After preparation of conventional PAP-smear specimens from the endocervical brush, the brush containing residual sample material was inserted into a sample collection vial (e.g. PP Vial by Sarstedt) containing 5 ml PST-buffer (PST buffer: 1% TRITON® X100 0.3% SDS, and phosphate buffered saline; the phosphate buffered saline contained Proclin300 as a preservative for stabilization of the buffer before use). The handle of the brush was removed and the brush tip was left within the sample collection vial. The sample collection vial with sample material and collecting brush was heat-treated within a period of time of 2 hours after collection of the sample, for 15 min at 95° C. in a water bath, alternatively 25 min at 100° C. in heating block could be used for heat treatment step.

A heating block with thermostat and with drills of appropriate size for vials (NeoLab Cat. No 2-2503) was used. Sample was stored without any further handling (no centrifugation, brush left in vial) at room temperature for up to 14 days until analysis of the sample by ELISA as follows:

Performing the ELISA $p16^{INK4a}$ level and/or concentration was determined in duplicate measurements taking 100 µl of sample/determination. Levels of $p16^{INK4a}$ were measured at for example 1 days, 2 days, 5 days and 6 days after start of storage of samples at room temperature. Each data point was a mean of 2 measurements (variation coefficients below 10%).

ELISA-plates coated with $p16^{INK4a}$ specific antibody clone mtm E6H4 were used for the ELISA detection of $p16^{INK4a}$. 100 µl of the lysed cell sample was added to each well. For purpose of calibration of the test, different concentrations of recombinant $p16^{INK4a}$ protein (0 pg/ml, 50 pg/ml, 100 pg/ml, 200 pg/ml, 400 pg/ml, 800 pg/ml) were included in the test. Samples were incubated for 1 h at room temperature.

Thereafter 3 washing steps were performed using an automated ELISA washer. Horse radish peroxydase (HRP) conjugated secondary antibody clone mtm D7D7 specific for $p16^{INK4a}$ protein was used for detection in the sandwich ELISA system. 100 µl of D7D7-HRP solution was added to each well and incubated for 1 h at room temperature. Thereafter 3 washing steps were performed using an automated ELISA washer. 100 µl of TMB-substrate was added to each well. The ELISA plates were incubated at 25° C. for exactly 15 min in the dark. Then the reaction was stopped by addition of 80 µl 2.5M $H_2SO_4$. Within 5 min after stopping the reaction, OD 450 nm was determined. After evaluation of the results, each sample returned a value for the OD. Using a calibration curve based on the calibration samples included in the assay the OD were transferred to relative Units/mL.

Ep-CAM and gCatenin were determined from analogous samples using specific sandwich-ELISA based on following antibody-pairs: HEA-125 (German Cancer Research Center) and MK1-410 (BioVendor) for Ep-CAM, 10F8 (mtm laboratories) and 4C12 (mtm laboratories) for gCatenin.

Results

The $p16^{INK4a}$ levels measured in the cervical specimens was reported either in OD (all data for one sample were obtained using only one ELISA plate) or in Units/mL. The levels measured in a respective sample at different points in time are shown in FIG. 1 for samples not treated with heat and in FIG. 2 for samples treated with heat.

Figure 2:
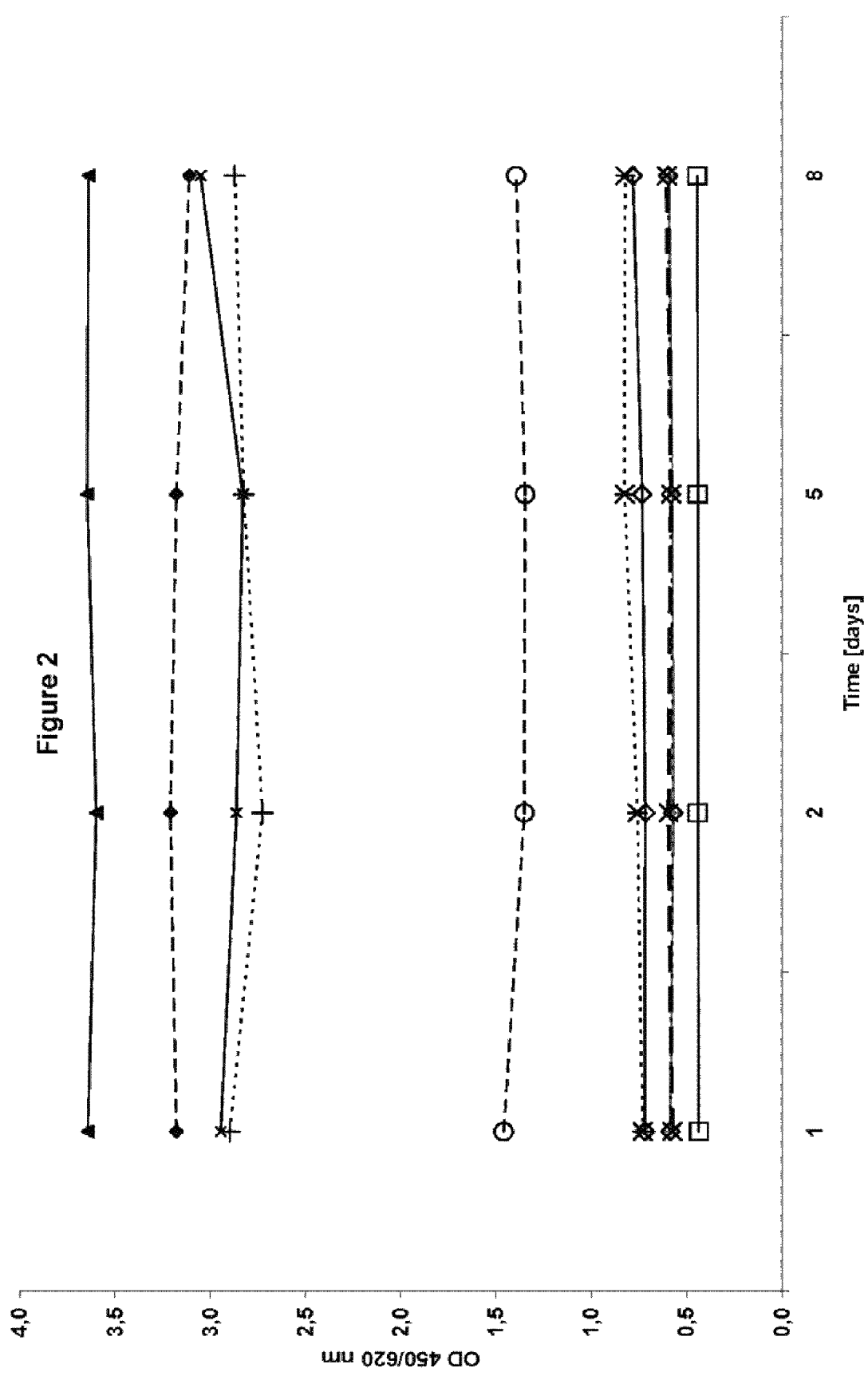
FIG. 2 shows the stability of $p16^{INK4a}$ in solubilized samples after heat treatment. The levels of $p16^{INK4a}$ were determined in samples from the human cervix uteri using an ELISA. The cervical samples were solubilized in a sample medium, heat treated in a water bath for 15 min at 95° C. and thereafter incubated for several days at ambient temperature. Aliquots from each sample were taken on day 1 (immediately after heat treatment), day 2, day 5 and day 8. The graph shows $p16^{INK4a}$ levels determined in 11 different patient samples and displays stability of $p16^{INK4a}$ upon heat treatment. For details see Example 1.

The data shown in FIG. 1 demonstrate that there was a significant loss of $p16^{INK4a}$ signal in the ELISA if a sample was stored at ambient temperature over a period of several days. This indicates that there was degradation of the p16$^{INK4a}$ analyte protein in the sample. In FIG. 2, the results show that there was no loss of signal over the whole period of time that the samples were subjected to heat treatment. Therefore, the level of p16$^{INK4a}$ from cervical specimen samples obtained after heat treatment was stabilized during total storage time.

In order to determine if the level of p16$^{INK4a}$ in specimen samples was affected by variation of the heat treatment procedure, 4 consecutive aliquots were taken from 14 different samples incubated as follows:

Aliquot 1 taken after 15 min at 100° C.
Aliquot 2 taken after 25 min at 100° C.
Aliquot 3 taken after 35 min at 100° C.
Aliquot 4 taken after further 10 min at 105° C. (total duration of heat treatment was 45 min)

Figure 3:
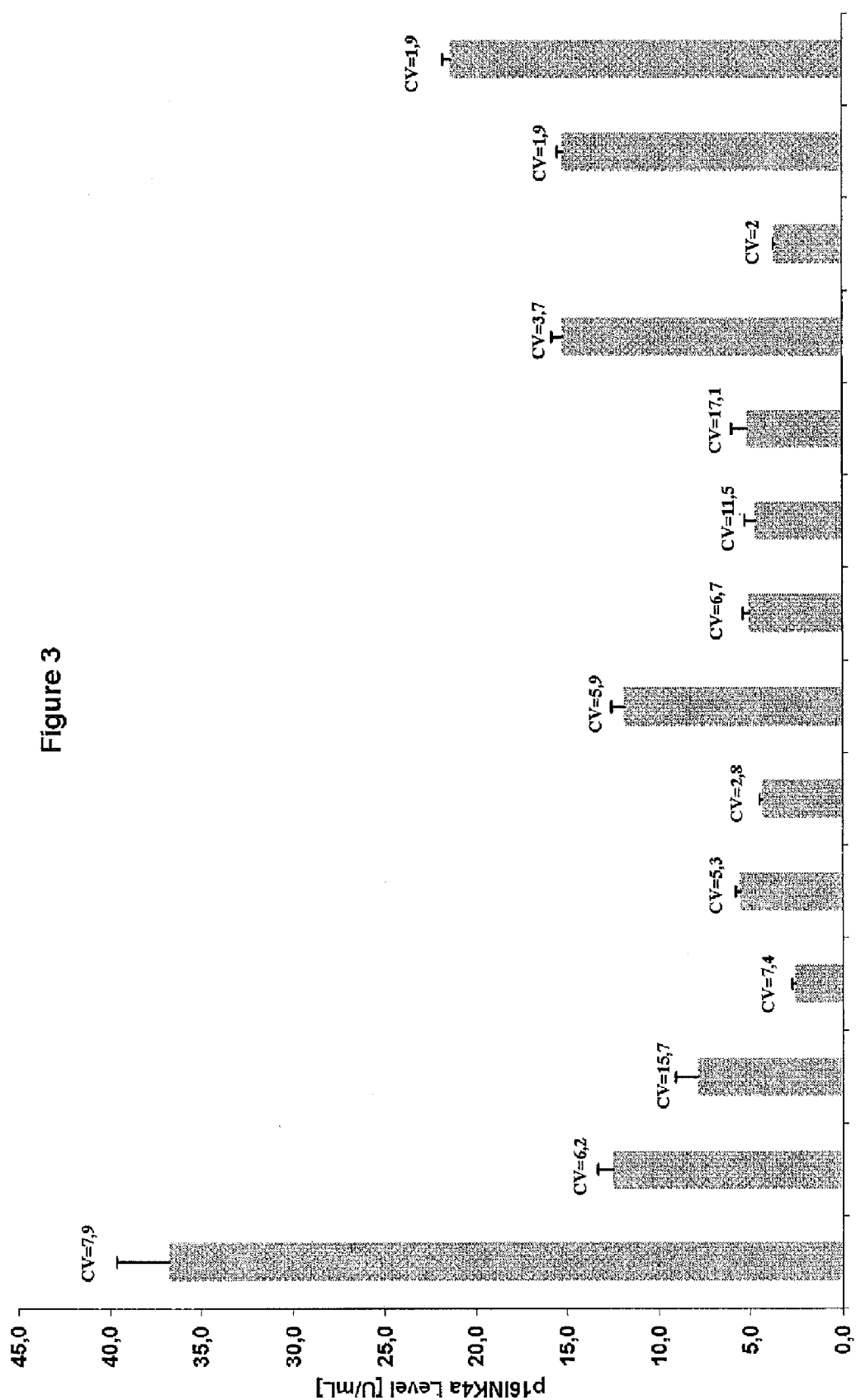
FIG. 3 shows the impact of the duration of the heat treatment on stability of $p16^{INK4a}$ in solubilized samples after heat treatment. The levels of $p16^{INK4a}$ were determined in samples from the human cervix uteri using an ELISA. 14 different cervical samples were incubated up to 45 min above 95° C. 4 consecutive aliquots were taken after 15 min, 25 min, 35 min and 45 min from start of heat treatment. The $p16^{INK4a}$ concentration was determined in duplicate from each aliquot separately, using the $p16^{INK4a}$ ELISA. Average concentration, including error bars of 4 determinations, as well as coefficient of variation between 4 determinations are shown. For details see Example 1.

The p16$^{INK4a}$ concentration was determined in duplicate from each aliquot separately, using the p16-ELISA. Average concentration, including error bars of 4 determinations, as well as coefficient of variation between 4 determinations, are given in FIG. 3. 4 U/mL were set as a limit of detection in the present circumstances. The results of this experiment show that no difference in p16$^{INK4a}$ levels was visible when samples were heat-treated for different lengths of time. This demonstrates that a wide range of time periods may be applied. Increased duration or even increased temperature for the heat treatment of samples did not interfere with the analyte determination using the p16-ELISA.

Figure 4:
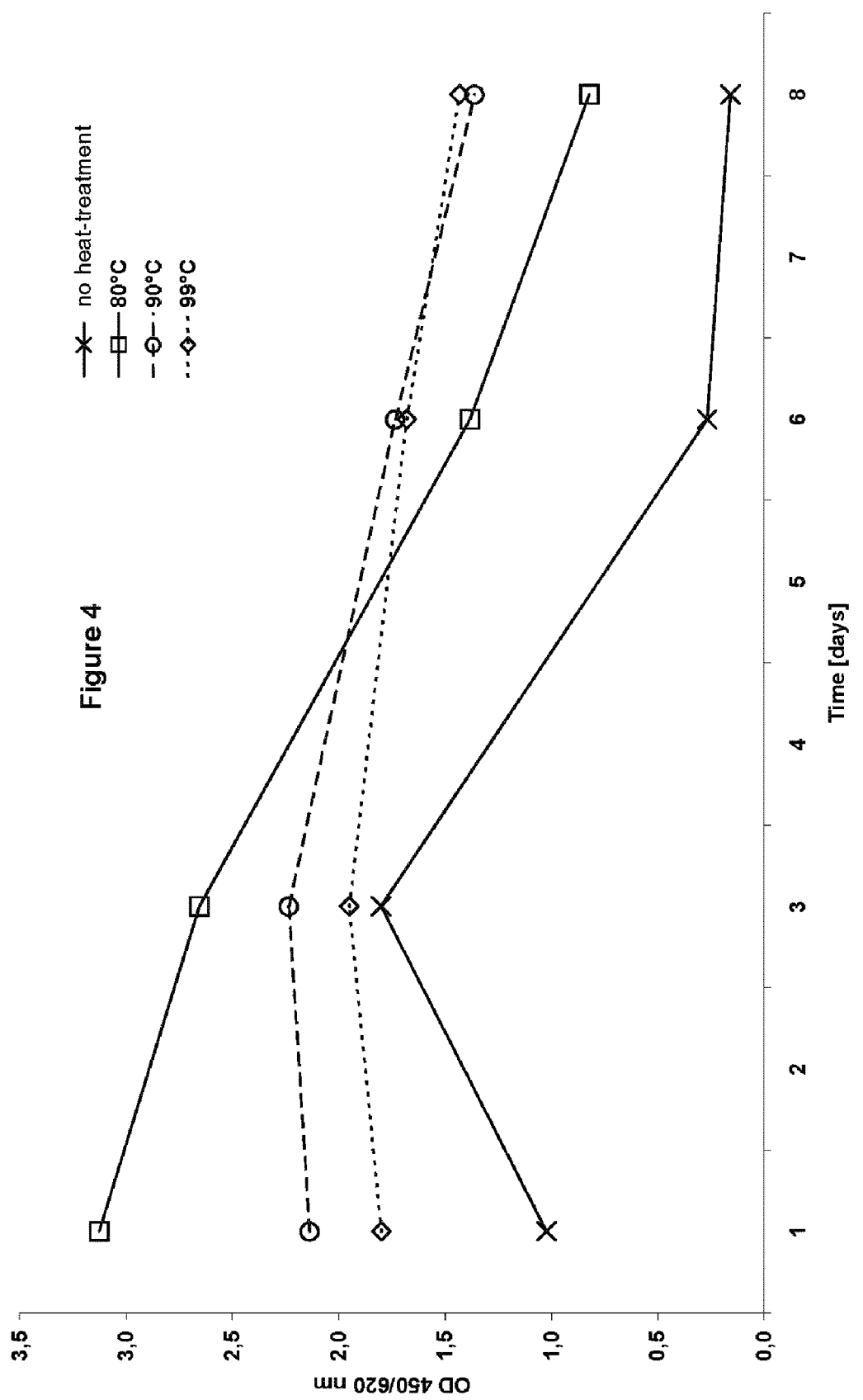
FIG. 4 shows the impact of the temperature applied during heat treatment on stability of $p16^{INK4a}$ in solubilized samples after heat treatment. The levels of $p16^{INK4a}$ were determined in samples from human cervix uteri using an ELISA. A mixed pool of several patient samples positive for $p16^{INK4a}$ was divided in 4 aliquots which were either left untreated or incubated for 10 min at 80° C., 90° C., 99° C., respectively. Aliquots were taken on day 1 (immediately after heat treatment), day 3, day 6 and day 8. For details see Example 1.

Treating a pool of several patient samples for 10 min at 80° C., 90° C. or 99° C. showed that the stabilization was dependent upon the temperature of heat treatment. An aliquot of the pooled samples was left untreated and used as a control. As shown in FIG. 4, the control was unstable when not subjected to heat treatment and was stabilized upon treatment temperatures. The observed stabilization was the best when the heat treatment was performed at a temperature above 90° C.

Figure 5:
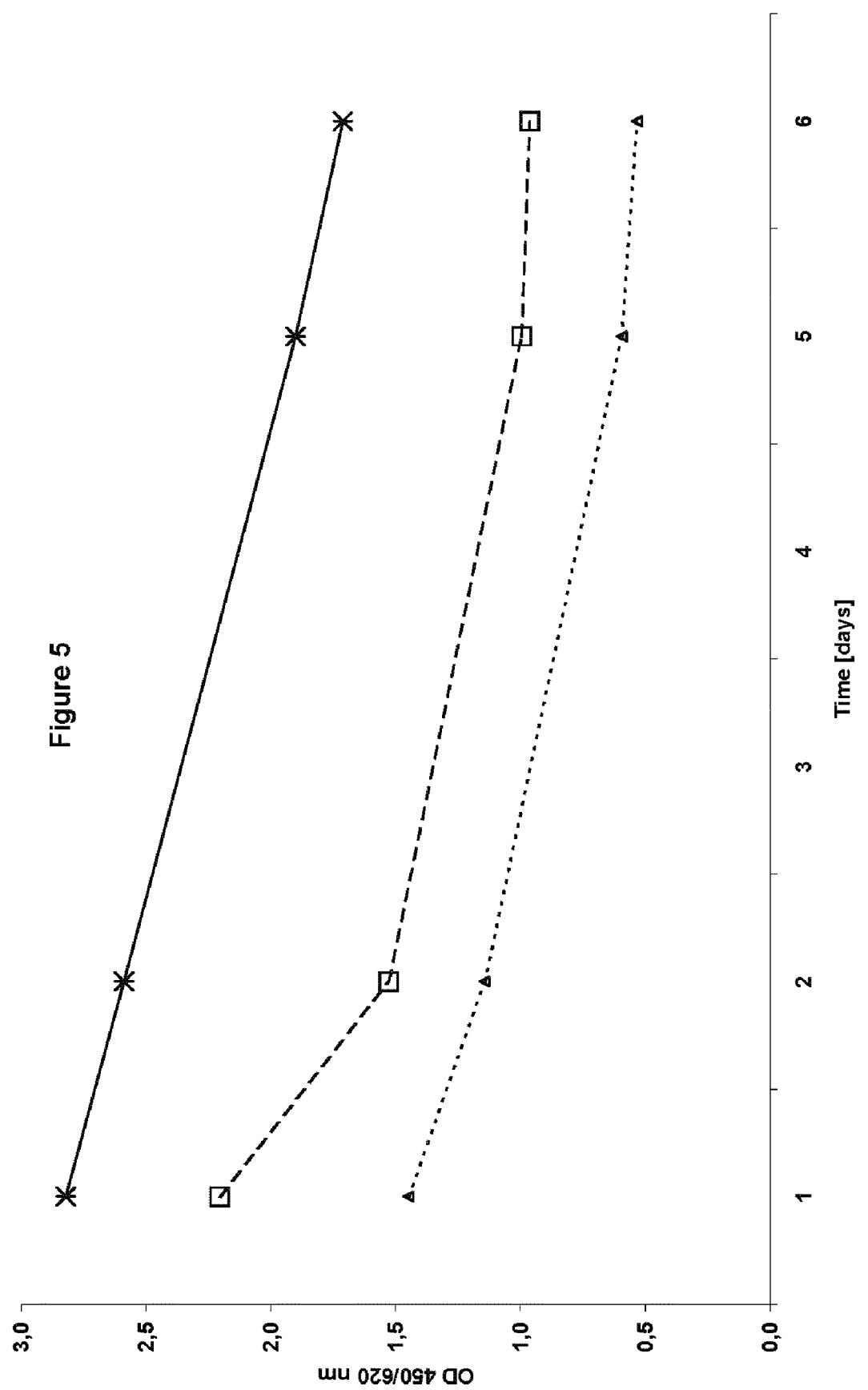
FIG. 5 shows the stability of gCatenin in six solubilized samples. The levels of gCatenin were determined in samples from the human cervix uteri using an ELISA. 3 Cervical samples were solubilized in sample medium immediately after the samples had been obtained and were incubated thereafter for several days at ambient temperature. Aliquots were taken on day 1 (immediately after heat treatment), day 2, day 5 and day 6. The levels of gCatenin determined in each sample using an ELISA are graphically represented. For details see Example 1.
Figure 6:
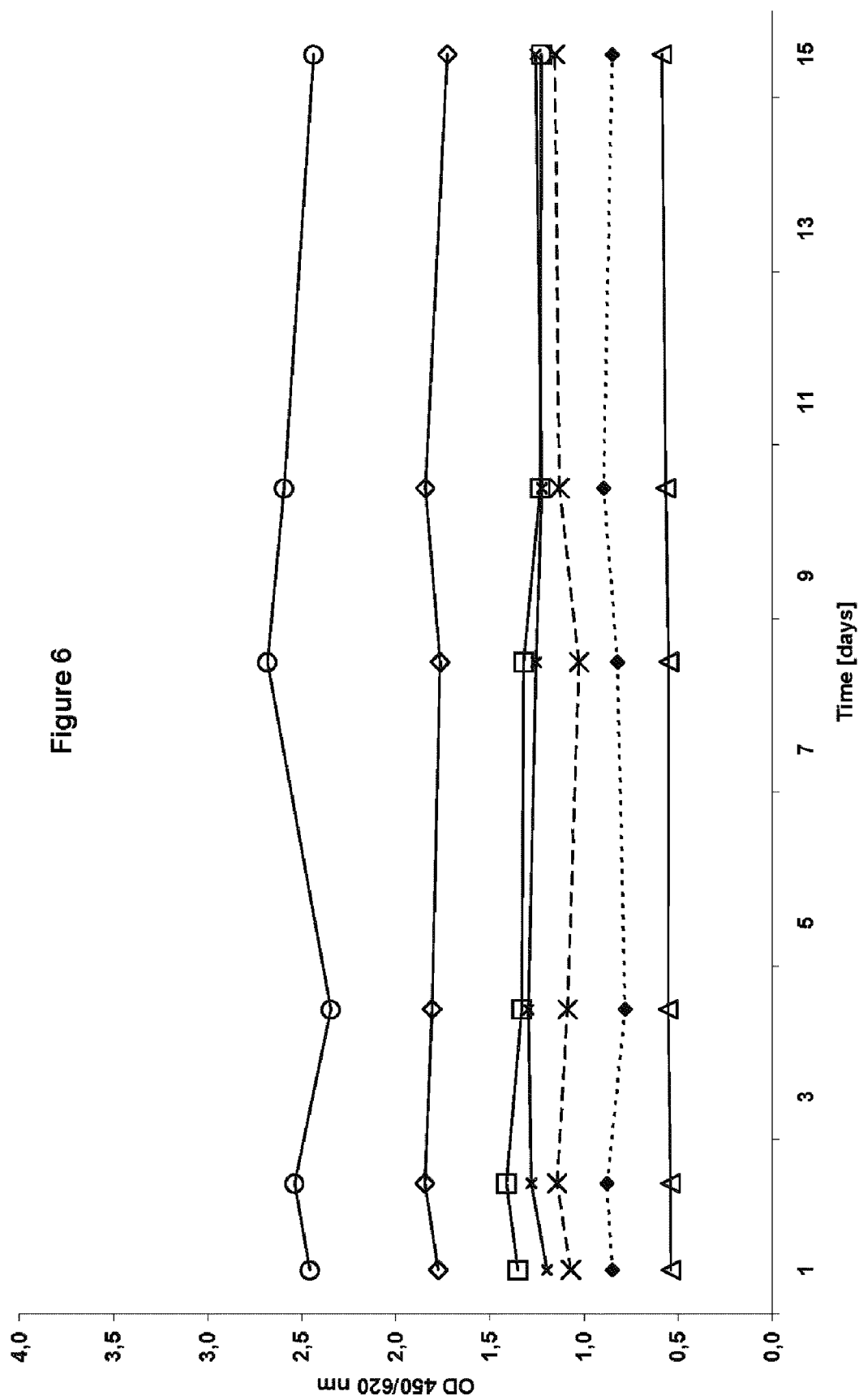
FIG. 6 shows the stability of gCatenin in seven solubilized samples after heat treatment. The levels of gCatenin were determined in samples from human cervix uteri using an ELISA. Seven Cervical samples were solubilized in sample medium immediately after the samples had been obtained, heat treated in a water bath for 15 min at 95° C. and were incubated thereafter for several days at ambient temperature. Aliquots were taken on day 1 (immediately after heat treatment), day 2, day 4, day 8, day 10 and day 15. For details see Example 1.

The results of gCatenin levels in 3 patient samples not treated by heat and 7 patient samples treated by heat are shown in FIGS. 5 and 6, respectively. Our results show that gCatenin was stabilized within the PST-buffer upon heat treatment.

Figure 7:
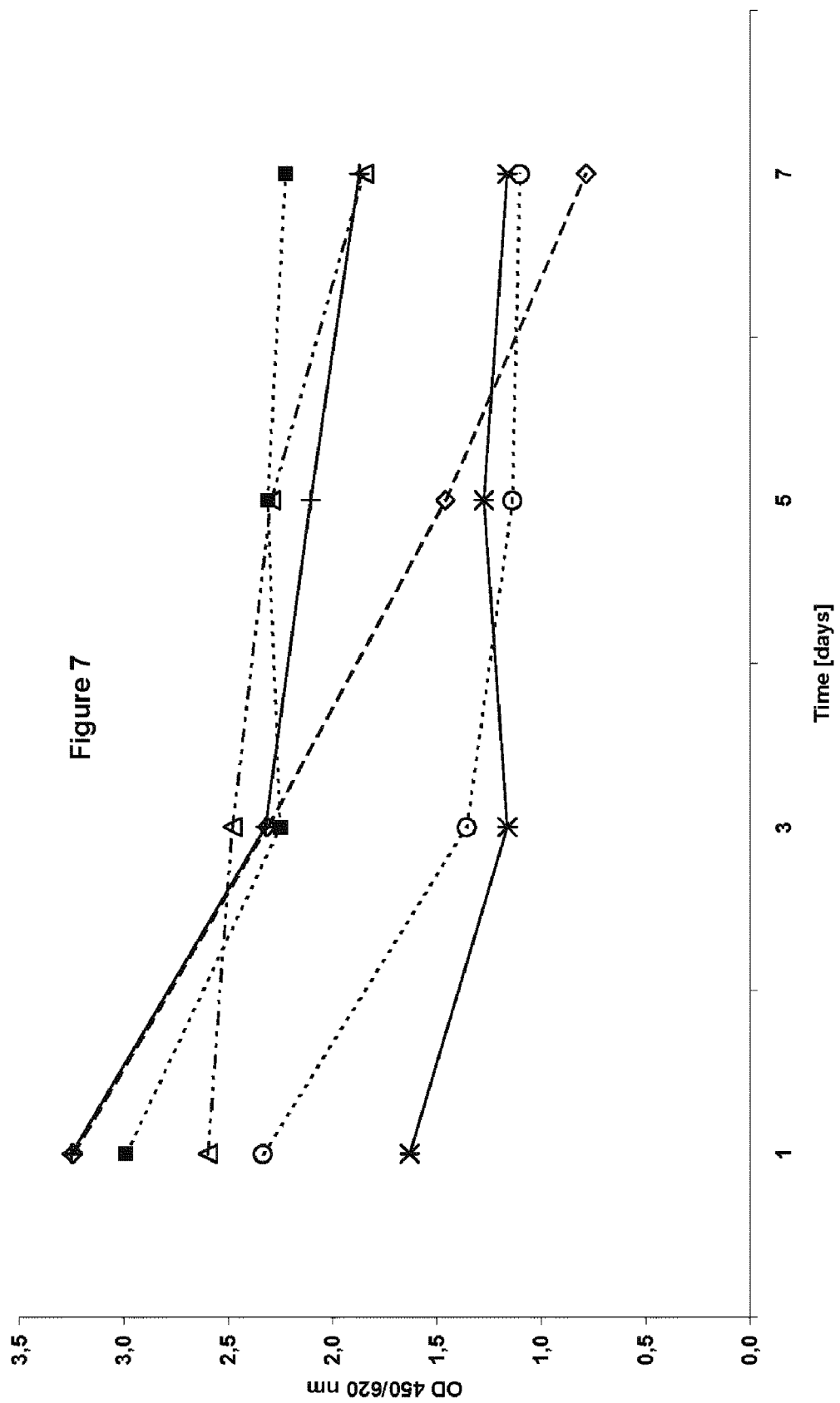
FIG. 7 shows the stability of Ep-CAM in seven solubilized samples. The levels of Ep-CAM were determined in samples from human cervix uteri using an ELISA. Six Cervical samples were solubilized in sample medium immediately after the samples had been obtained and were incubated thereafter for several days at ambient temperature. Aliquots were taken on day 1 (immediately after heat treatment), day 3, day 5 and day 7. For details see Example 1.
Figure 8:
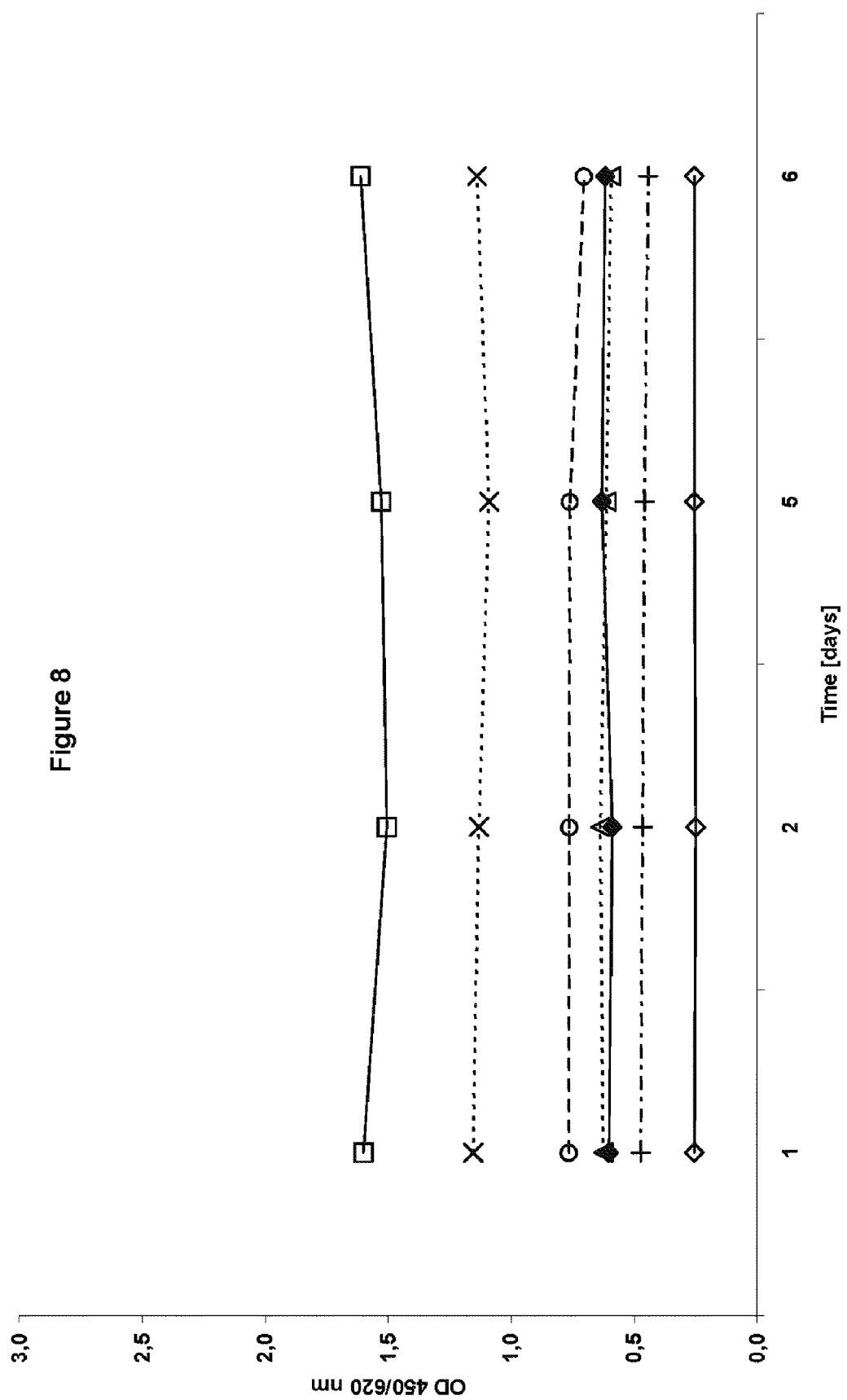
FIG. 8 shows the stability of Ep-CAM in seven solubilized samples after heat treatment. The levels of Ep-CAM were determined in samples from human cervix uteri using an ELISA. 7 Cervical samples were solubilized in sample medium immediately after the samples had been obtained, heat treated in a waterbath for 15 min at 95° C. and were incubated thereafter for several days at ambient temperature. Aliquots were taken on day 1 (immediately after heat treatment), day 2, day 5 and day 6. For details see Example 1.

Analogous results of Ep-CAM levels in 6 patient samples not treated by heat and 7 patient samples treated by heat are shown in FIGS. 7 and 8, respectively. Our results indicate that Ep-CAM was also stabilized within the PST-buffer upon heat treatment.

Determination of p16$^{INK4a}$ was performed from aliquots taken from the same patient samples as the determination of Ep-Cam and gCatenin. The determination of p16$^{INK4a}$ was performed using distinct ELISA plates for each analyte. However, it is possible to generate ELISA plates where determination of two or more analytes is performed on one single plate.

In summary, the results of the outlined experiments show that a temperature applied during heat treatment was well suited above 90° C. for at least 5 min under the given conditions. Furthermore, extension of the treatment duration up to 45 min did not alter the analytes. Furthermore, the results show that stability of p16, gCatenin and Ep-CAM analytes were achieved for storage at ambient temperature at least 6 days. The observed stabilization was not protein specific, because it was observed for 3 different proteins.

The results also demonstrate that all analytes tested in the experiment could be detected in an immunoassay, wherein the first incubation step was performed in the presence of 0.3% SDS and 1% TRITON® X100.

It can be noted that the heat treatment procedure resulted in a standardization of the extraction procedure of p16$^{INK4a}$ from cells present in a patient sample. Due to the presence of the brush, which was left in the vial during the heat treatment, an efficient lysis of the cells and a homogeneous solubilization of analytes was achieved by heat treatment. The risk of loosing material left in the brush was greatly reduced.

Example 1a

Figure 9:
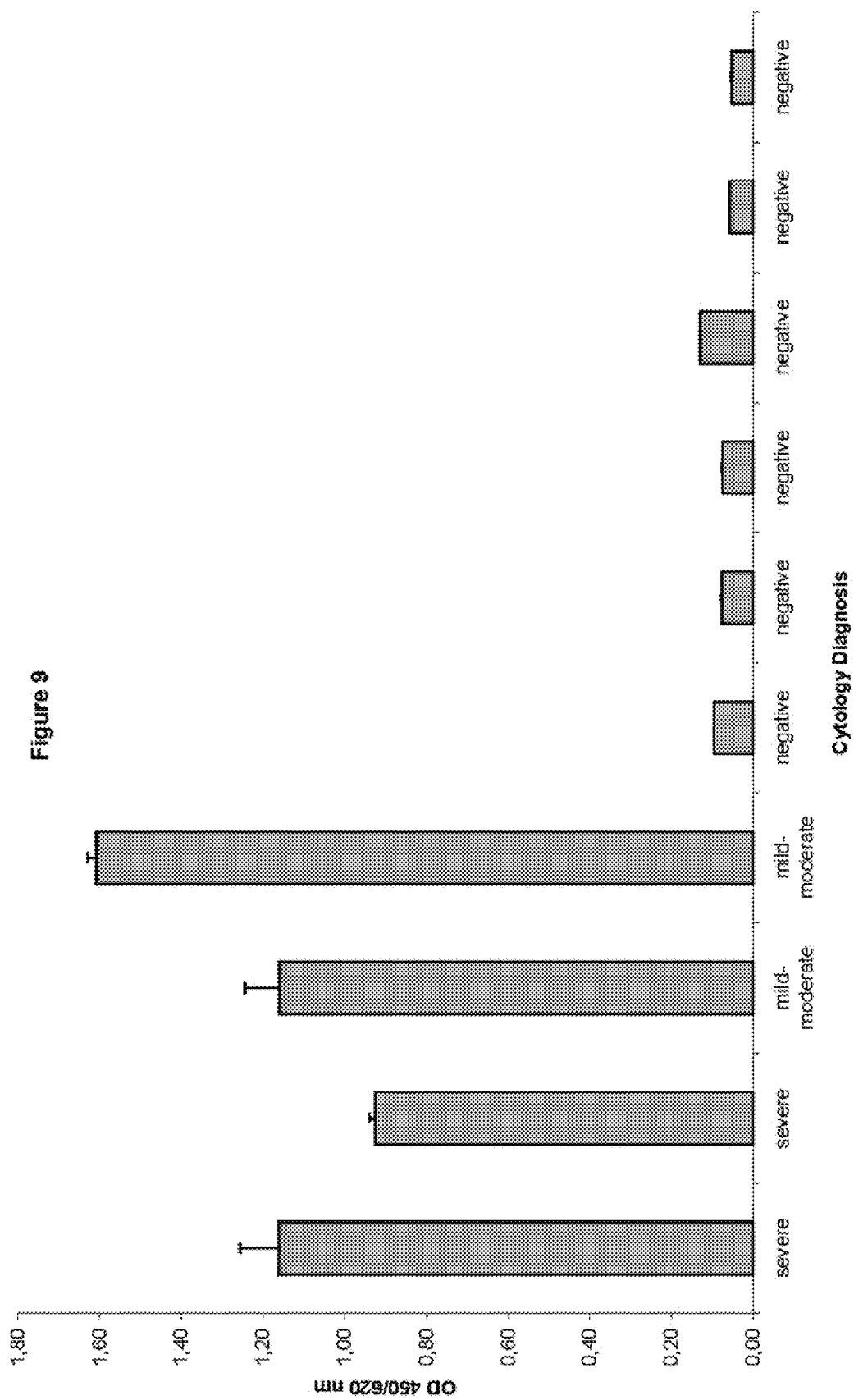

Denaturing Immunoassay for p16$^{INK4a}$ Protein in Samples from the Uterine Cervix In a variation to the protocol shown above, the inventors performed various experiments with different heating times and different compositions of sample media. Cervical sampling device (CYTOBRUSH®) containing cervical swab was introduced into a 1.5 ml reaction tube containing 700 µl of lysis buffer (PBS with 3% TRITON® X100; 0.5% SDS). The shaft was cut and the closed tube was vortexed for 30 seconds at room temperature. Thereafter, brush was removed. Reaction tube was heated for 30 min at 95° C. 100 µl of lysate was pipetted per well in a 96 well plate coated with p16$^{INK4a}$ capture antibody (clone E6H4). Detection was performed with biotinylated p16$^{INK4a}$-specific detection antibody and Streptavidin-HRP conjugate. DAB was used as substrate. The results are displayed in FIG. 9. It can be seen that p16$^{INK4a}$ was detected by the ELISA assay in the presence of denaturing agents (0.5% SDS and 3% TRITON® X100). Moreover, there was correlation between the elevated p16$^{INK4a}$ values (indicative for p16$^{INK4a}$ overexpression) and the cytologically confirmed presence of an abnormality of the tissue tested.

Example 2

Performance of Denaturing Immunoassays for p16$^{INK4a}$ Using ELISA and LIA Technique The levels of p16$^{INK4a}$ protein are determined in cervical specimens that are obtained with a standard cervical sampling device. 12 samples are subjected to a heating step according to the invention disclosed herein, and are analysed for the level of p16$^{INK4a}$ by ELISA and LIA technique in the presence of high detergent concentrations.

Sample preparation and stabilization and ELISA are performed as shown in Example 1.
Performing the LIA
Dynabeads M-280 are coated using the standard coating procedure from Dynal with the p16$^{INK4a}$ specific antibody clone mtm E6H4 and stored in a concentration of 5 mg/ml in storage buffer. Antibody clone mtm D7D7 specific for p16$^{INK4a}$ is labelled with isoluminol by a standard procedure. The assay is performed with the DIASORIN LIAISON® analyzer. 200 µl sample of the lysed cell sample is added to 100 µl tracersolution (monoclonal anti-p16$^{INK4a}$ antibody D7D7 labelled with isoluminol in 10 mM PBS pH 7.4, 1% BSA) and 20 µl antibody-coated magnetic particles. After 10 min incubation at 37° C., the particles are separated with a magnet and washed for three times with LIAISON® Wash/System Liquid. After the third wash step, the particles are separated again and the supernatant is discarded. The chemiluminescent signal is generated by injection of two ready-to-use trigger solutions (LIAISON® Starter Kit). For purpose of calibration of the test, different concentrations of recombinant p16$^{INK4a}$ protein (0 pg/ml, 50 pg/ml, 100 pg/ml, 200 pg/ml, 400 pg/ml, 800 pg/ml) are included in the test.

Results

The p16$^{INK4a}$ levels measured in the cervical specimens are reported in Units/mL.

Figure 10:
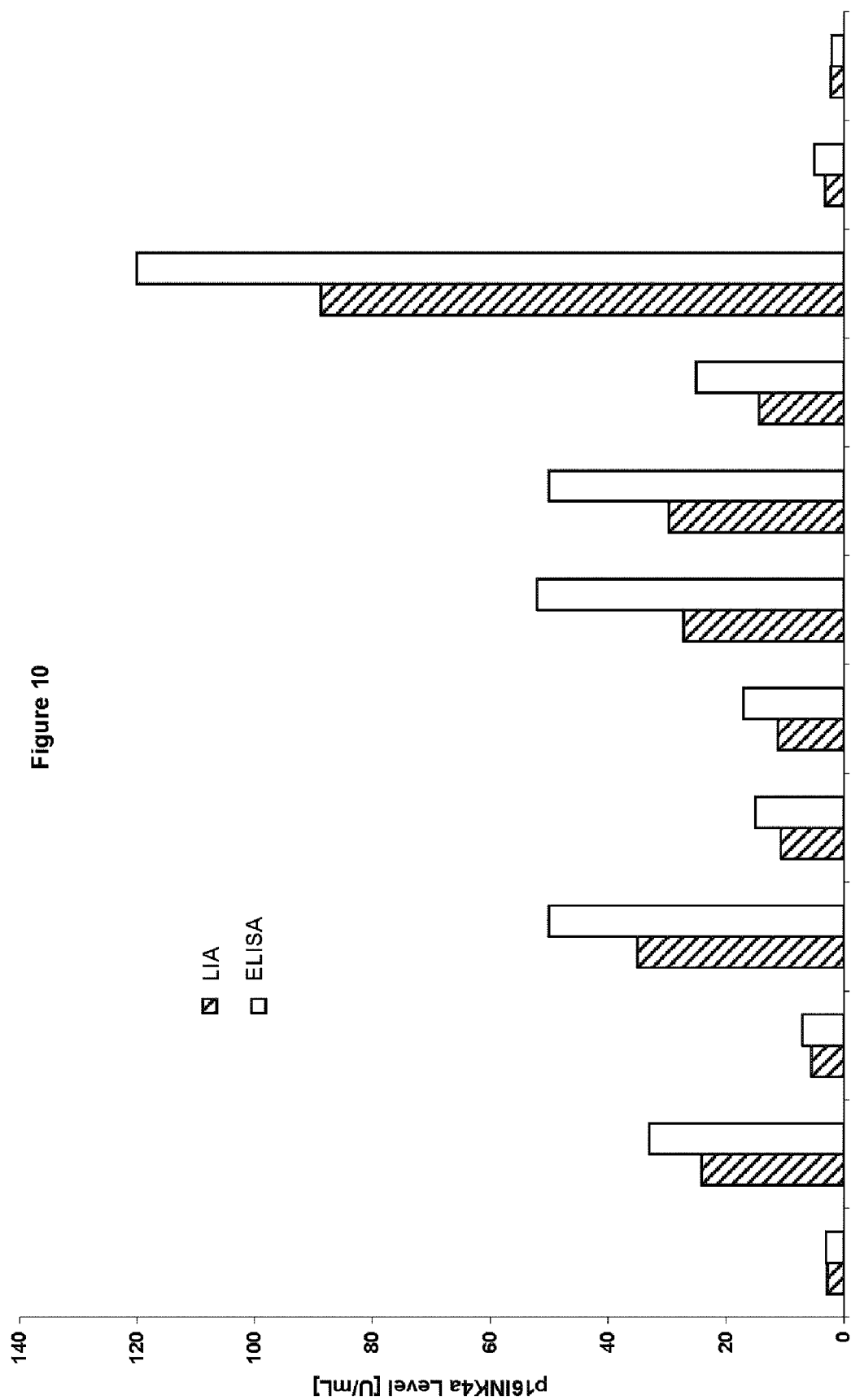
FIG. 10 shows the p16$^{INK4a}$ levels determined in patient samples by ELISA and LIA; both performed in the presence of 0.3% SDS. The p16$^{INK4a}$ levels were determined in samples from human cervix uteri using ELISA and LIA immunoassays. Immunoassay was performed in the presence of 0.3% SDS for both assay types. 12 Cervical samples were solubilized in sample medium immediately comprising 0.3% SDS. Samples within the sample medium were directly applied to the immunoassay. Both types of immunoassay prove to detect p16$^{INK4a}$ protein levels in the presence of elevated concentration of SDS. For details see Example 2.

The data shown in FIG. 10 show only minor differences in the p16$^{INK4a}$ levels measured by both assay types. The experiment thus proves that ELISA and LIA techniques may be used to detect the analyte in the presence of the denaturing agent in a concentration (0.3% SDS) that allows to uphold the denatured status of the analyte protein.

Inventors show in further experiments that ELISA assay as well as LIA assay are equally performed for detection of several analytes (including p16$^{INK4a}$, gCatenin, Ep-Cam, HPV E7, CA19-9, MCM-2 and CDC-6), which may be detected reproducibly in the presence of significantly higher concentrations of denaturing agents, e.g., in the presence of 1% SDS. Alternatively a concentration of 3% TRITON® X100 is successfully used in an ELISA format for the detection of analytes. In these cases, the inventors observe an improvement of reproducibility of the results generated by analysis of samples in immunoassay when denaturing agents are present during the assay compared to cases where denaturing agents are omitted. This indicates that denaturing agents in the range of concentrations as detailed herein are suited to improve the performance and especially the reproducibility of immunochemical detection methods.

Example 3

Detection of Cervical Intraepithelial Neoplasia in an Lateral Flow Test Format 9 cervical swabs (conditions of lysis were similar to those of Example 1) were subjected to conventional PAP testing and to lysis, in subsequent lateral flow based detection of overexpression of cyclin dependent kinase inhibitor p16$^{INK4a}$ in solutions prepared from the cells contained in the swabs. The lateral flow testing was performed as follows:

Cell Lysis

Cervical swab samples were transferred to sample collection vial (SCV) containing 5 ml of PST-buffer. The sample collection vial was incubated in the water bath for 15 min at 95° C. The sample collection vial was cooled down to room temperature, and 4 ml of the supernatant were transferred without centrifugation to a fresh tube.

Performing the Lateral Flow Assay

Applying Capture Antibody to Membrane

Stock solutions of p16$^{INK4a}$ specific antibody clone mtm E6H4 and recombinant p16$^{INK4a}$ protein were separately diluted in TBS (containing 1% bovine serum albumin) to give two ready-to-use spotting solutions each with a final antibody concentration of 1 mg/ml or final recombinant p16$^{INK4a}$ concentration of 10 µg/ml. The two ready-to-use solutions were spotted onto different locations of nitrocellulose membrane at 30 µl/30 cm.

Schleicher&Schuell wicks were attached to one end of the nitrocellulose and the dipsticks were dried for 15 min at 37° C. Then they were allowed to equilibrate at room temperature and cut into 4 mm width dipsticks.

Incubation with Samples

2 µl of p16$^{INK4a}$ specific antibody (clone mtm D7D7), conjugated to colloidal gold (40 nm particle size; OD 44) was added to 100 µl of each sample lysate (comprising 0.3% SDS and 1% TRITON®), mixed well and transferred to a microtiter well. Dipstick, coated with clone E6H4 as capture antibody line and recombinant p16$^{INK4a}$ as positive control line, was added to the well containing sample, soaked and run to completion. The signal was read whilst dipstick was still wet.

Results

Figure 11:
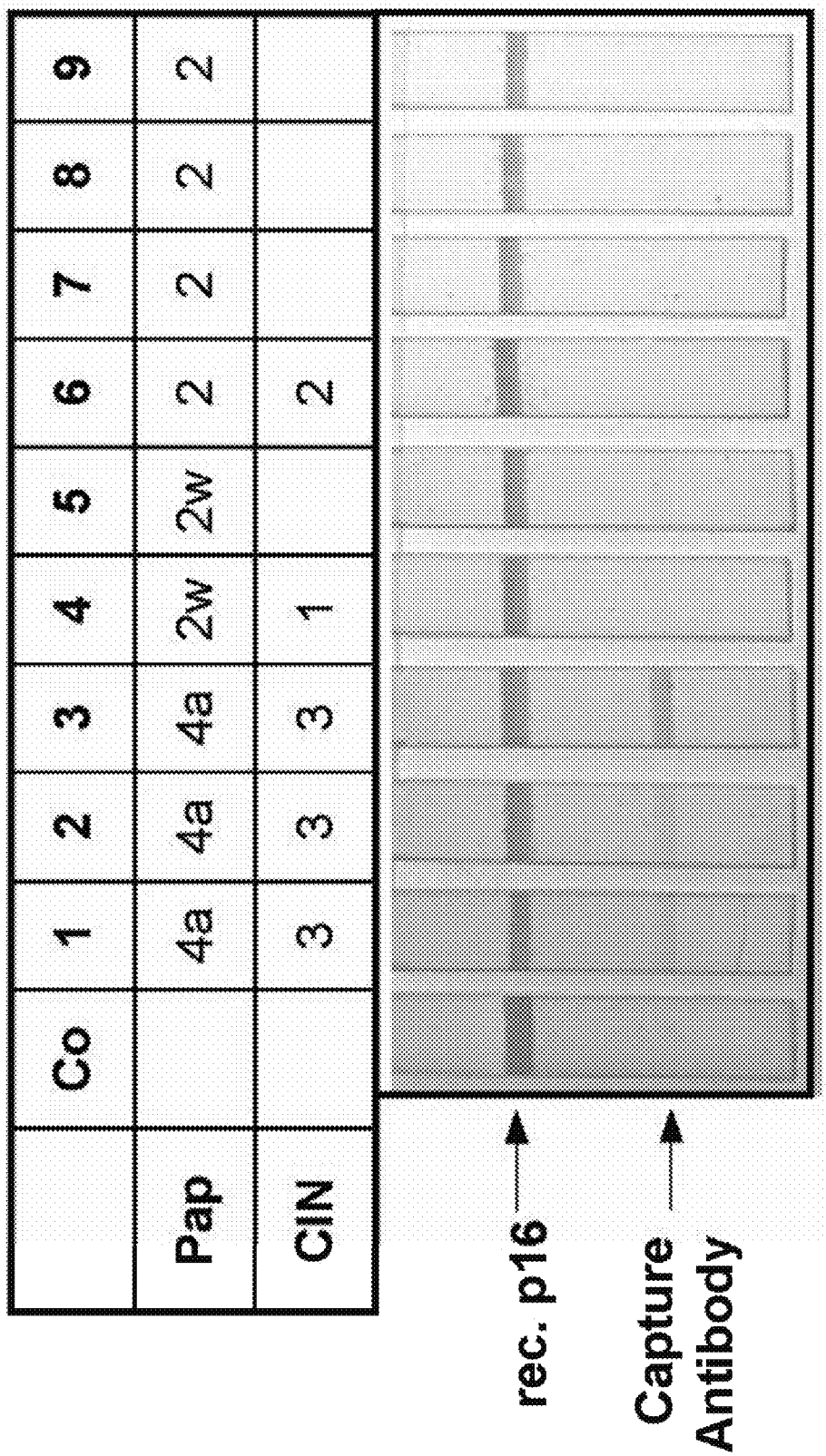
FIG. 11 shows the p16$^{INK4a}$ levels determined in patient samples by Lateral Flow assay performed in the presence of 0.3% SDS. Table representing data were obtained for Cytology and Histology specimens from patients in correlation to the representation of the results obtained when applying the sample solution comprising 0.3% SDS and 1% TRITON® X100 directly to the Lateral flow dipstick. It could be seen that in the dipstick assay format p16$^{INK4a}$ as correspond to severed dysplastic lesions in patients may be detected by generation of a specific band. This demonstrates that the dipstick format may be applied according to the present invention in the presence of denaturing agents. For details see Example 3.

The results are shown in FIG. 11. In our testing format, all 3 samples classified as PAP IVa by PAP staining of a corresponding cytological specimen and therefore representing dysplastic cells, gave clearly visible bands in the area of spotted capture antibody. In contrast, no bands were detected for residual 6 samples, classified as PAP II-IIw by PAP staining, and therefore representing normal cells. Positive control lines indicated functional test components. Negative control (Co) without sample did not show nonspecific staining.

Example 4

Immunochemical Analysis of Protein Levels of MCM-5 and MCM-2 in Liquid Based Cytology Samples from Urine 20 LBC samples of urine cells in CytoLyt™ are used for the present example. Protein analysis is performed in an ELISA format as given in Example 1 using pairs of commercially available antibodies directed against the respective analyte proteins. In both cases, monoclonal antibodies are used as capture antibodies coated to the ELISA plates and polyclonal antibodies are used as detection antibodies. Experimental procedures are performed as given in there.

In this example, the body samples are analysed for the analytes immediately after lysis and heating the samples.

It can be shown that MCM-5 as well as MCM-2 are easily detected in lysates from urine LBC samples after lysis of such samples in the sample medium as disclosed in Example 1 and after heating of the sample solutions. The results obtained by the immunochemical assay on MCM-2 and MCM-5 correspond well to the results obtained from immunocytochemical analysis of the samples for the respective proteins. In cytology, immuno-cytological staining for MCM-5 protein is used as aid in assessment of diagnosis.

The experiments above demonstrate that the methods disclosed herein are suited for stabilization of a wide range of analytes for storage and transportation and subsequent analysis by immunoassay without the need for preservative additions. Furthermore the experiments demonstrate that denaturing immunoassays apply to a wide range of analytes and can help to improve the immunochemical detection thereof.

The present invention facilitates easy and cost effective preservation of analytes obtained from a mammalian body for subsequent analysis by immunochemical analysis. The invention provides a method that obviates the use of toxic and hazardous ingredients that may otherwise be used for preservation of the analytes in the samples. Furthermore, the present invention allows for increased accuracy and reproducibility of determination of analytes in samples and thus increases reliability of immunochemical detection methods. Therefore, the invention contributes to improved immunochemical methods that contribute to test results supporting the assessment of diagnosis of diseases in humans.

What is claimed is:

1. A method for preparing and stabilizing one or more analytes in solutions for a denaturing immunoassay of body samples, comprising the steps of:
   i) obtaining a solubilized mammalian body sample containing one or more analytes in a sample medium comprising a denaturing agent of SDS at 0.1-1% (w/w), wherein the one or more analytes are HPV (human papilloma virus) associated markers;

ii) subsequently heating said sample medium containing the one or more analytes to a temperature of 90-110±2° C. for a period of time of 3 to 45 minutes;

iii) stabilizing and storing the one or more heated analytes in said sample medium; and iv) subsequently performing a denaturing immunoassay on said sample medium containing the one or more analytes and the denaturing agent of SDS.

2. The method according to claim 1, wherein said HPV associated markers are derived from HPV genes L1, L2, E1, E2, E4, E5, E6 or E7.

3. The method according to claim 1, wherein said storing is carried out at 2-30° C.

4. The method according to claim 1, wherein said storing is carried out for 1, 2, 5, or 6 days.

5. The method according to claim 1, wherein said storing is carried out for up to 14 days.

6. The method according to claim 1, wherein said sample medium of (iii) is stored without further handling until subsequently performing the denaturing immunoassay.

7. A method for detecting one or more analyte proteins by an immunoassay, comprising the steps of:

i) bringing a sample comprising the one or more analyte proteins into contact with a sample medium comprising a denaturing agent of SDS at 0.1-1% w/v;

ii) heating said sample in the sample medium at a temperature of 90-110±2° C. for a period of time of 3-45 minutes to denature the one or more analyte proteins; and iii) performing one or more immunoassays for detection of the one or more analyte proteins using the sample of (ii) as a specimen for the immunoassays, wherein said analyte proteins are HPV (human papilloma virus) associated markers.

8. The method according to claim 7, wherein the immunoassay is selected from the group consisting of immunoprecipitation assays, immunological assays, EIA, ELISA, RIA, lateral flow assays, flow through assays, immunochromatographic strips, and latex agglutination assays.

9. The method according to claim 7, wherein the SDS is present in a concentration of 0.3% w/v or higher in the sample medium.

10. The method according to claim 7, wherein the temperature is between 95° C. and 99° C.

11. The method according to claim 7, wherein the period of time is at least 5 minutes.

12. The method according to claim 7, wherein the period of time is between 7 minutes and 30 minutes.

13. The method according to claim 7, wherein the period of time is between 10 minutes and 27 minutes.

14. The method according to claim 1, wherein the period of time is between 20 and 25 minutes.

15. The method according to claim 1, wherein the heating step is performed in a heating device selected from the group consisting of a water bath, a pressure cooker, a microwave oven, an UV heating device, and a heating block.

16. The method according to claim 1, wherein the sample is selected from the group consisting of secretions, swabs, lavages, body fluids, semen, cell- and tissue-samples, liquid based cytology samples, blood, smears, sputum, urine, stool, liquor cerebrospinalis, bile, gastrointestinal secretions, lymph, bone marrow, aspirates and biopsies of organs.

17. The method according to claim 1, wherein said HPV associated markers are derived from HPV genes L1, L2, E1, E2, E4, E5, E6 or E7.

18. The method according to claim 1, further comprising a step between the steps (ii) and (iii): storing the sample medium at 2-30° C. for up to 14 days.

19. The method according to claim 18, wherein the sample is stored for 1, 2, 5, or 6 days.

20. The method according to claim 18, wherein said sample medium of (ii) is stored without further handling until subsequently performing the denaturing immunoassay.

21. The method according to claim 1, wherein the temperature is between 95° C. and 99° C.

22. The method according to claim 1, wherein the period of time is at least 5 minutes.

23. The method according claim 1, wherein the period of time is between 7 minutes and 30 minutes.

24. The method according to claim 23, wherein the period of time is between 10 minutes and 27 minutes.

25. The method of claim 24, wherein the period of time is between 20 and 25 minutes.

\* \* \* \* \*